US005792929A

United States Patent [19]
Mariani et al.

[11] Patent Number: 5,792,929
[45] Date of Patent: Aug. 11, 1998

[54] PLANTS WITH MODIFIED FLOWERS

[75] Inventors: Célestina Mariani, Heusden; Jan Leemans, Deurle; Willy De Greef, Gent, all of Belgium

[73] Assignee: Plant Genetic Systems, N.V., Gent, Belgium

[21] Appl. No.: 466,125

[22] Filed: Jun. 6, 1995

Related U.S. Application Data

[62] Division of Ser. No. 395,649, Feb. 28, 1995, Pat. No. 5,689,041, which is a continuation of Ser. No. 214,045, Mar. 15, 1994, abandoned, which is a continuation of Ser. No. 671,752, Mar. 21, 1991, abandoned.

[30] Foreign Application Priority Data

Aug. 10, 1989 [EP] European Pat. Off. ......... 89 402 270.6

[51] Int. Cl.$^6$ .................. A01H 5/00; A01H 5/10; A01H 1/02; A01H 1/04; C12N 15/29; C12N 15/31; C12N 15/32; C12N 15/55; C12N 15/82

[52] U.S. Cl. .................. 800/205; 800/250; 800/DIG. 13; 800/DIG. 14; 800/DIG. 16; 800/DIG. 17; 800/DIG. 23; 800/DIG. 24; 800/DIG. 26; 800/DIG. 38; 800/DIG. 40; 800/DIG. 41; 800/DIG. 43; 800/DIG. 44; 800/DIG. 46; 800/DIG. 55; 800/DIG. 56; 800/DIG. 57; 800/DIG. 58; 800/DIG. 59; 800/DIG. 62; 47/58; 47/DIG. 1; 536/23.2; 536/23.6; 536/23.7; 536/23.71; 536/24.1; 435/69.1; 435/69.8; 435/172.3; 435/199; 435/320.1; 435/418; 435/419

[58] Field of Search .................. 800/205, 250, 800/DIG. 17, DIG. 43; 47/58, DIG. 1; 435/320.1, 240.4, 419, 69.1, 199, 69.8, 418, 172.3, DIG. 13, DIG. 14, DIG. 17, DIG. 16, DIG. 23, DIG. 24, DIG. 26, DIG. 38, DIG. 40, DIG. 41, DIG. 43, DIG. 44, DIG. 46, DIG. 55–DIG. 59, DIG. 62; 536/23.2, 24.1, 23.71, 23.6, 23.7

[56] References Cited

U.S. PATENT DOCUMENTS 5,356,799   10/1994   Fabijanski et al. ............... 435/172.3

FOREIGN PATENT DOCUMENTS

| 0 272 144 | 6/1989 | European Pat. Off. . |
| 0 329 308 | 8/1989 | European Pat. Off. . |
| 0 344 029 | 11/1989 | European Pat. Off. . |
| 88/09334 | 12/1988 | WIPO . |
| 89/09262 | 10/1989 | WIPO . |
| 90/08828 | 8/1990 | WIPO . |
| 90/08830 | 8/1990 | WIPO . |

OTHER PUBLICATIONS

*Breeding Field Crops*, Third Edition, 1987, Poehlman, AVI Publishing Co., Inc., Wesport, CT., pp. 129–147.

Xie et al., in: *Advances in Gene Technology: Molecular Genetics of Plants and Animals*, Miami Winter Symposia, vol. 20, Downey et al., (ed.), 1983, Academic Press, NY, NY p. 593.

Yakovlev et al. 1995, FEBS Letters 366: 156–158.

*Primary Examiner*—David T. Fox
*Attorney, Agent, or Firm*—Burns, Doane, Swecker & Mathis, LLP

[57] ABSTRACT

A plant, the nuclear genome of which is transformed with a foreign DNA sequence encoding a product which neutralizes the activity of another product which disrupts the metabolism, functioning and/or development selectively of the plant's flower cells, particularly reproductive organ cells, or seed cells or embryo cells. The foreign DNA sequence also optionally encodes a marker.

90 Claims, 4 Drawing Sheets

```
         ↓
        ATCG                                        10         20         30         40         50         60         70
GGAGCCGCAC ATGAAAAAAG CAGTCATTAA CGGGGAACAA ATCAGAAGTA TCAGCCGACCT CCACCAGACA
           ↑
                80         90        100        110        120        130        140
        TTGAAAAAGG AGCTTGCCCT TCCGGAATAC TACGGTGAAA ACCTGGACGC TTTATGGGAT TGTCTGACCG 150        160        170        180        190        200        210
        GATGGGTGGA GTACCCGCTC GTTTGGAAT GGAGGCAGTT TGAACAAAGC AAGCAGCTGA CTGAAAATGG 220        230        240        250        260        270        280
        CGCCGAGAGT GTGCTTCAGG TTTTCCGTGA AGCGAAAGCG GAAGGCTGCG ACATCACCAT CATACTTTCT 290        300        310        320        330        340
        TAATACGATC AATGGGAGAT GAACAATATG GAAACACAAA CCCGCAAGCT TGGTCTAGAG

FIG. 2
```

PLANTS WITH MODIFIED FLOWERS

This application is a divisional, of application Ser. No. 08/395,649 filed Feb. 28, 1995, now U.S. Pat. No. 5,689, 041, which is a continuation of U.S. Pat. application Ser. No. 08/214,045, filed Mar. 15, 1994, now abandoned, which is a continuation of U.S. application Ser. No. 07/671,752 filed Mar. 21, 1991, now abandoned, which is based on PCT application Ser. No. EP 90/01315 filed Aug. 9, 1990, which derives priority from European Patent Application No. 89 402 270.6 filed Aug. 10, 1989.

FIELD OF THE INVENTION

This invention relates to a method of restoring fertility to a transgenic nuclear male-sterile or female-sterile plant by crossing such a sterile plant with a transgenic fertility-restorer plant to provide a transgenic fertility-restored plant having a foreign DNA sequence from the nuclear genome of the restorer plant that is stably integrated into the nuclear genome of the restored plant. The foreign DNA sequence of this invention contains a foreign DNA (hereinafter the "fertility-restorer DNA") that: 1) encodes a first RNA, protein or polypeptide which, when produced or overproduced in a cell of a flower, particularly a male or female reproductive organ thereof, or a seed or an embryo of the restored plant, prevents the activity in the flower, seed or embryo cell of a second RNA, protein or polypeptide which, when produced or overproduced in the flower, seed or embryo cell, would otherwise significantly disturb adversely the metabolism, functioning and/or development of the flower, seed or embryo cell; and 2) is in the same transcriptional unit as, and under the control of, a first promoter which is capable of directing expression of the fertility-restorer DNA at least in the same flower or seed or embryo cells of the restored plant where the second RNA, protein or polypeptide is being produced or overproduced. The second RNA, protein or polypeptide is encoded by a foreign "sterility-DNA" that is from the nuclear genome of the sterile plant, that is also stably integrated into the nuclear genome of the restored plant and that is under the control of a "sterility-promoter" which is capable of: i) directing expression of the sterility DNA selectively in specific cells of each flower, particularly at least one male or at least one female reproductive organ thereof, or each seed or each embryo of the restored plant and ii) thereby rendering the restored plant male- or female-sterile in the absence of expression of the fertility-restorer DNA in the specific flower, seed or embryo cells.

The foreign DNA sequence of this invention, transferred from the restorer plant into the restored plant, is optionally a foreign chimaeric DNA sequence that can also contain a second foreign DNA (the "first marker DNA") that: 1) encodes a third RNA, protein or polypeptide which, when present at least in a specific tissue or specific cells of the plant, renders the entire plant easily separable or distinguishable from other plants that do not contain the third RNA, protein or polypeptide at least in the specific tissue or specific cells of the plant; 2) is in the same transcriptional unit as, and under the control of, a second promoter which is capable of directing expression of the first marker DNA in at least specific tissue or specific cells of the plant; and 3) is in the same genetic locus of the nuclear genome of the restored plant as the fertility-restorer DNA.

This invention also relates to a foreign chimaeric DNA sequence that contains at least one fertility-restorer DNA under the control of at least one first promoter and that can also contain, adjacent to the fertility-restorer DNA(s) and the first promoter(s), at least one first marker DNA under the control of at least one second promoter.

This invention further relates to: a vector that contains the foreign DNA sequence of this invention and is suitable for the transformation of a plant cell, whereby the foreign DNA sequence is stably integrated into the nuclear genome of the cell; the resulting fertility-restorer plant cell; cultures of such fertility-restorer plant cells; a fertility-restorer plant and its reproductive material (e.g., seeds) which can be regenerated from such a fertility-restorer plant cell and the nuclear genome of which contains, stably integrated therein, the foreign DNA sequence; a fertility-restored plant and its reproductive material containing, stably integrated in their nuclear genome, the foreign DNA sequence, together with at least one sterility DNA under the control of at least one sterility promoter; and a cell of the fertility-restored plant, as well as cultures thereof.

This invention yet further relates to a process is for producing the restorer plant and its reproductive material by transforming a cell of the plant with the foreign DNA sequence whereby the fertility-restorer DNA is: 1) under the control of the first promoter and optionally in the same genetic locus as the first marker DNA under the control of the second promoter; and 2) stably integrated into the nuclear genome of the plant's cells.

The invention further relates to hybrid seeds produced by crossing: 1) the restorer plant, preferably also containing, stably integrated in its nuclear genome, the first marker DNA encoding a protein conferring a resistance to an herbicide on the restorer plant; with 2) a nuclear male- or female-sterile plant which has, stably integrated in its nuclear genome a) the sterility DNA under the control of the sterility promoter and, adjacent to the sterility DNA, preferably within the same genetic locus of the nuclear genome, b) a second marker DNA, encoding a fourth RNA, protein or polypeptide and preferably also conferring an herbicide resistance on the sterile plant, under the control of a third promoter capable of directing expression of the second marker DNA in at least a specific tissue or specific cells in which expression of the second marker DNA renders the plant easily separable or distinguishable from those in which there is not such expression. This invention particularly relates to such hybrid seeds as produced on a commercial scale, preferably in a substantially random population, with increased efficiency of cross-pollination and without the need for extensive hand-labor.

BACKGROUND OF THE INVENTION

Hybridization of plants is recognized as an important process for producing offspring having a combination of the desirable traits of the parent plants. The resulting hybrid offspring often have the ability to outperform the parents in different traits, such as in yield, adaptability to environmental changes, and disease resistance. This ability is called "heterosis" or "hybrid vigor". As a result, hybridization has been used extensively for improving major crops, such as corn, sugarbeet and sunflower. For a number of reasons, primarily related to the fact that most plants are capable of undergoing both self-pollination and cross-pollination, the controlled cross-pollination of plants without significant self-pollination, to produce a harvest of hybrid seeds, has been difficult to achieve on a commercial scale.

In nature, the vast majority of crop plants produce male and female reproductive organs on the same plant, usually in close proximity to one another in the same flower. This favors self-pollination. Some plants, however, are exceptions as a result of the particular morphology of their reproductive organs which favors cross-pollination. These plants produce hybrid offspring with improved vigor and adaptability. One such morphology in *Cannabis ssp.* (hemp) involves male and female reproductive organs on separate plants. Another such morphology in *Zea mays* (corn) involves male and female reproductive organs on different parts of the same plant. Another such morphology in *Elaeis guineensis* (oilpalm) involves male and fertile female gametes which become fertile at different times in the plant's development.

Some other plant species, such as *Ananas comosus* (pineapple), favor cross-pollination through the particular physiology of their reproductive organs. Such plants have developed a so-called "self-incompatibility system" whereby the pollen of one plant is not able to fertilize the female gamete of the same plant or of another plant with the same genotype.

Some other plant species favor cross-pollination by naturally displaying the so-called genomic characteristic of "male-sterility". By this characteristic, the plants' anthers degenerate before pollen, produced by the anthers, reaches maturity. See: "Male-Sterility in Higher Plants", M. L. H. Kaul, 1987, in: Monographs on Theoretical and Applied Genetics 10, Edit. Springer Verlag. Such a natural male-sterility characteristic is believed to result from a wide range of natural mutations, most often involving deficiencies, and this characteristic cannot easily be maintained in plant species that predominantly self-pollinate, since under natural conditions, no seeds will be produced.

Some types of naturally occurring male-sterility are cytoplasmatically encoded, while others are nuclear encoded. One type of male-sterility is the result of a combination of both nuclear encoded male-sterility and cytoplasmatically encoded male-sterility. The male-sterility inducing nuclear alleles are usually recessive, and only plants that contain the male-sterility cytoplasmic allele and that are homozygous for the male-sterility inducing nuclear allele are phenotypically male-sterile. In this type of plant, corresponding dominant male-fertility inducing alleles or "fertility restorers" produce a male-fertile phenotype. As a result, the male-sterile offspring of this type of plant can be made male-fertile by pollinating the male-sterile plants with pollen containing the fertility restorers. As a result, the offspring of plants of this type are of commercial value where the economic product is seeds (e.g., for plants such as corn, sorghum and sunflower).

Most of the known naturally occurring male-sterility genes and their corresponding fertility-restorer genes have not been used in breeding or production of new varieties for essentially two reasons: a) insufficient quality of the genes responsible for the male-sterility and restoration characteristics; and b) low cross-pollination capability of the crops in which they occur.

1. The quality of the genes

To realize the full potential of a male-sterility/fertility-restorer system, several quality requirements have to be achieved:

a) Stability of the genes encoding the male-sterility under a broad range of different environmental conditions. Most of the currently known systems, whether they are nuclear or cytoplasmatically encoded, do not display sufficient stability. As a consequence of this, under some unpredictable climatological conditions, self-pollination occurs within the plants, and heterogeneous offspring are harvested. According to seed certification requirements, not more than 1% of non-hybrid seed is tolerated for most major field crops.

b) No side effects on the plants. Many cytoplasmic male-sterility genes induce a decrease in plant vigor. This can be tolerated up to a certain level, if the hybrid vigor effect offers a significant improvement of the crop compared to the negative effect. Another side effect which has been observed in crops carrying male-sterility genes consists of an enhanced sensitivity to some plant pathogens (e.g., corn plants carrying T-cytoplasmic male-sterility are highly susceptible to *Helminthosporium maydis* infections). Restorer genes also often display negative side effects although these are usually not due to the genes themselves but to genes closely linked to the restorer genes. These side effects consist, in most cases, of an increased disease or pest susceptibility or a decreased quality of the crop.

2. Efficiency of cross-pollination

Reasonably efficient cross-pollination is essential for the production of hybrid seeds at an acceptable cost. For major field crops that are poorly adapted to cross-pollination, it is unrealistic to assure crops-pollination by hand. Therefore, it has been envisaged to sell, as a commercial product, not the F1 hybrid, but the selfed $F_2$ offspring thereof (e.g., cotton and wheat). The disadvantage of this method lies, however, in the loss of homogeneity and heterosis and the segregation of specific useful gene combinations. To assure high yield of a crop by a farmer, it is advantageous that hybrid crops be fully fertile (with the exception of very efficient cross-pollinating species such as corn and oilseed rape). This is particularly the case with crops that form heavy or sticky pollen which is not easily transported by wind (e.g., cotton), with crops that are not attractive to pollinating insects (e.g., wheat) and with crops which display cleistogamy (e.g., soybean).

SUMMARY OF THE INVENTION

In accordance with this invention, a transgenic fertility-restored plant is provided, in which the nuclear genome contains, stably integrated therein, a foreign DNA sequence, preferably a foreign chimaeric DNA sequence, characterized by:

(a) a fertility-restorer DNA encoding a first RNA, protein or polypeptide which, when produced or overproduced in a cell of a flower, particularly a male or female organ thereof, a seed or an embryo of the plant, prevents the activity in the flower, seed or embryo cell of a second RNA, protein or polypeptide that, when produced or overproduced in the flower, seed or embryo cell, could otherwise significantly disturb the metabolism, functioning and/or development of the flower, seed or embryo cell; the second RNA, protein or polypeptide being encoded by a sterility DNA that is also stably integrated into the nuclear genome of the plant and is under the control of a sterility promoter capable of directing expression of the sterility DNA selectively in specific cells of each of the plant's flowers, particularly a male or female organ thereof, and/or seeds and/or embryos and of thereby rendering the plant male-sterile or female-sterile in the absence of expression of the fertility-restorer DNA in the specific flower, seed and/or embryo cells; and (b) a first promoter capable of directing expression of the fertility-restorer DNA at least in the specific flower, seed and/or embryo cells of the plant where the sterility promoter directs gene expression of the sterility DNA; the fertility-restorer DNA being in the same transcriptional unit as, and under the control of, the first promoter.

The foreign DNA sequence in the nuclear genome of the restored plant can also comprise, preferably in the same genetic locus as the fertility-restorer DNA:

(c) a first marker DNA encoding a third RNA, protein or polypeptide which, when present at least in a specific tissue or specific cells of the plant, renders the plant easily separable or distinguishable from other plants which do not contain the third RNA, protein or polypeptide at least in the specific tissue or specific cells; and (d) a second promoter capable of directing expression of the first marker DNA at least in the specific tissue or specific cells; the first marker DNA being in the same transcriptional unit as, and under the control of, the second promoter.

Also in accordance with this invention is provided a foreign chimaeric DNA sequence that comprises the fertility-restorer DNA and the first promoter and that can also comprise the first marker DNA and the second promoter, as well as at least one additional DNA encoding a transit peptide capable of transporting the first protein-or polypeptide or the third protein or polypeptide into a chloroplast or mitochondrion of a plant cell in which the foreign chimaeric DNA sequence is expressed in its cytoplasm.

Further in accordance with this invention is provided a method for providing the transgenic fertility-restored plant by crossing: a transgenic male-sterile or female-sterile plant, the nuclear genome of which contains, stably integrated therein, the sterility DNA under the control of the sterility promoter and preferably a second marker DNA under the control of a third promoter; with a transgenic fertility-restorer plant having a nuclear genome in which is stably integrated the foreign DNA sequence comprising the fertility-restorer DNA under the control of the first promoter and preferably the first marker DNA under the control of the second promoter.

Still further in accordance with this invention are provided: a cell of the transgenic fertility-restorer plant, as well as cell cultures consisting thereof, which are transformed with the foreign DNA sequence and can be used to regenerate the fertility-restorer plant; a cell of the transgenic fertility-restored plant, as well as cultures consisting thereof; and a process for obtaining hybrid seeds which grow into the transgenic fertility-restored plant by crossing the transgenic fertility-restorer plant with the transgenic male- or female-sterile plant carrying the sterility DNA under the control of the sterility promoter.

BRIEF DESCRIPTION OF THE DRAWINGS

FIG. 2 shows the DNA sequence of the barstar gene, used in Example 1, and indicates the mutated sequence of its ClaI site.

DETAILED DESCRIPTION OF THE INVENTION

Figure 1:
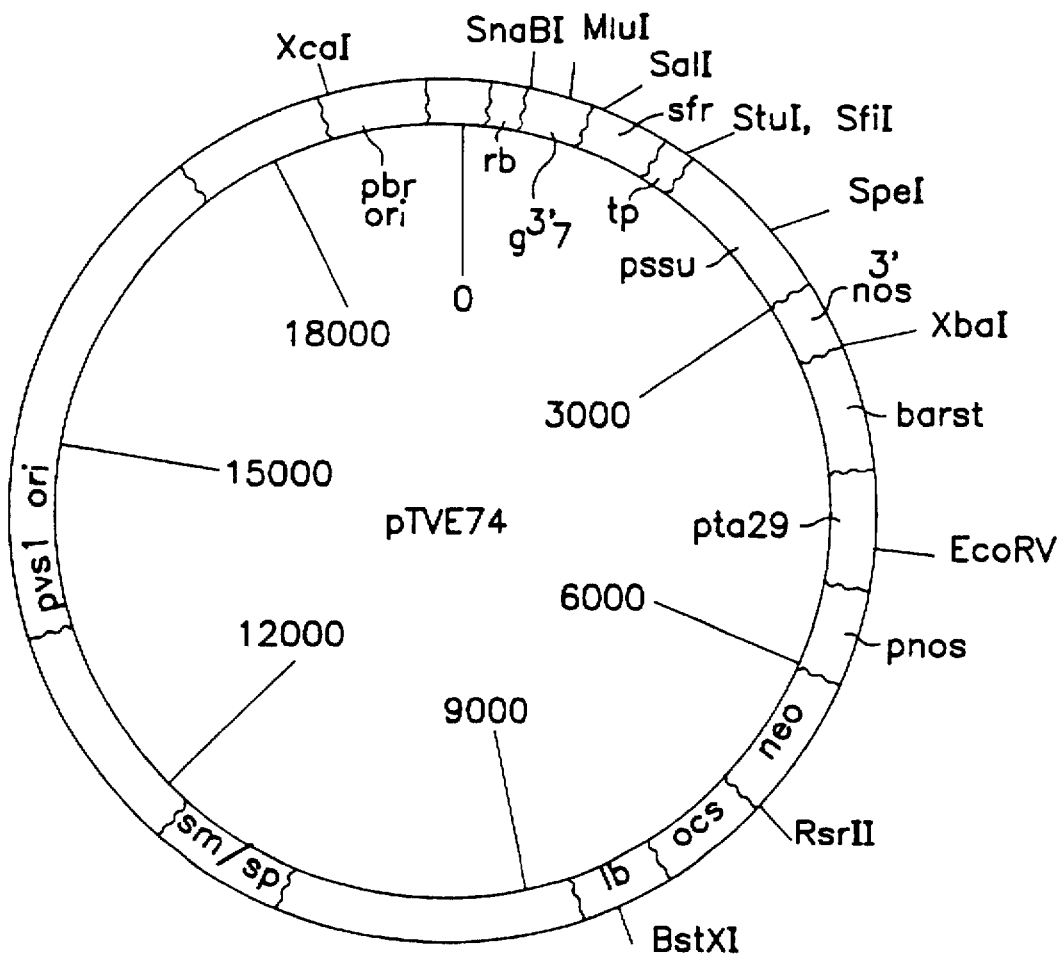
FIG. 1 shows a map of the vector pTVE74 of Example 1.

In accordance with this invention, a fertility-restorer plant is produced from a single cell of a plant by transforming the plant cell in a well known manner to stably insert, into the nuclear genome of the cell, the foreign DNA sequence of this invention. The foreign DNA sequence comprises at least one fertility-restorer DNA that is under the control of, and fused at its 5' end to, the first promoter and is fused at its 3' end to suitable transcription termination (or regulation) signals, including a polyadenylation signal. Thereby, the first RNA, protein or polypeptide is produced or overproduced in cells of at least each of the restorer plant's flowers, preferably one or more male or one or more female reproductive organs thereof, and/or seeds and/or embryos, so that when the restorer plant is crossed with a nuclear male-sterile or nuclear female-sterile plant, hybrid male-fertile female-fertile offspring are obtained. The foreign DNA sequence can also comprise at least one first marker DNA that is under the control of, and is fused at its 5' end to, the second promoter and is fused at its 3' end to suitable transcription termination signals, including a polyadenylation signal. The first marker DNA is preferably in the same genetic locus as the fertility-restorer DNA, whereby the third RNA, protein or polypeptide is produced in at least the specific tissue or specific cells of the fertility-restorer plant so that the plant can be easily distinguished and/or separated from other plants that do not contain the third RNA, protein or polypeptide in the specific tissue or specific cells. This guarantees, with a high degree of certainty, the joint segregation of both the fertility-restorer DNA and the first marker DNA into offspring of the plant.

The cell of a plant (particularly a plant capable of being infected with Agrobacterium) is preferably transformed in accordance with this invention, using a vector that is a disarmed Ti-plasmid containing the foreign DNA sequence and carried by Agrobacterium. This transformation can be carried out using procedures described, for example, in European patent publications 0,116,718 and 0,270,822. Preferred Ti-plasmid vectors contain the foreign DNA sequence between the border sequences, or at least located to the left of the right border sequence, of the T-DNA of the Ti-plasmid. Of course, other types of vectors can be used to transform the plant cell, using procedures such as direct gene transfer (as described, for example, in European patent publication 0,223,247), pollen mediated transformation (as described, for example, in European patent publication 0,270,356, PCT publication WO85/01856, and European patent publication 0,275,069), in vitro protoplast transformation (as described for example, in U.S. Pat. No. 4,684, 611), plant RNA virus-mediated transformation (as described, for example, in European patent publication 0,067,553, and U.S. Pat. No. 4,407,956) and liposome-mediated transformation (as described, for example, in U.S. Pat. No. 4,536,475).

Preferably, a fertility-restorer plant of this invention is provided by transforming a plant cell with a disarmed Ti-plasmid vector containing the foreign DNA sequence with a fertility-restorer DNA under the control of a first promoter and optionally a first marker DNA under the control of a second promoter. The marker DNA can be upstream or downstream of the fertility-restorer DNA in the Ti-plasmid vector, but preferably, the two are adjacent to one another and are located between the border sequences or at least located to the left of the right border sequence of the Ti-plasmid vector, so that they are properly transferred together into the nuclear genome of the plant cell. However, if desired, the cell can initially be transformed with the foreign DNA sequence containing the fertility-restorer DNA and the first promoter and can subsequently be transformed with the marker DNA and the second promoter, inserted into the same genetic locus in the cell's nuclear genome as the fertility-restorer DNA, or this transformation can be carried out vice versa. Suitable vectors for this purpose are the same as those discussed above for transforming cells with the foreign DNA sequence. The preferred vector is a disarmed Ti-plasmid vector.

The selection of the fertility-restorer DNA of this invention is not critical but is dependent on the selection of, and must correspond to, the sterility DNA which is responsible for the male- or female-sterility characteristic to be restored. In particular, the production or overproduction of the first RNA, protein or polypeptide encoded by the fertility-restorer DNA has to neutralize, block, offset, overcome or otherwise prevent the specific activity of the second RNA, protein or polypeptide encoded by the sterility DNA in flower cells, preferably cells of at least one male or at least one female reproductive organ, or in seed cells or in embryo cells of the restored plant. Examples of male- and female-sterility DNAs, to which the fertility-restorer DNAs of this invention must correspond, and the action of which they must counteract, are described in U.S. Pat. Nos. 5,652,354 and 5,633,441, respectively, which are incorporated herein by reference. A suitable fertility-restorer DNA can be selected and isolated in a well-known manner to overcome the effects of the sterility DNA in any cell of a flower, particularly a male or female organ, a seed and/or an embryo, in which the sterility promoter causes the sterility DNA to be expressed.

Preferred examples of fertility-restorer DNAs encode: barstar which neutralizes the activity of barnase (which degrades RNA molecules by hydrolyzing the bond after any guanine residue); EcoRI methylase which prevents the activity of the endonuclease EcoRI; or protease inhibitors which neutralize the activity of proteases, such as a papain (e.g., papain zymogen and papain active protein).

Another example of a fertility-restorer DNA is an antisense DNA (as described, for example, in European patent publication 0,223,399) which encodes a strand of DNA complementary to a strand of DNA that encodes a sterility DNA transcribed in an otherwise sterile plant's flower, seed or embryo cells, under the control of a sterility promoter. Such an antisense DNA can be transcribed into an RNA sequence capable of binding to the coding and/or non-coding portion(s) of a "sterility RNA", produced in the flowers seeds and/or embryos as a result of the expression of the sterility DNA, so as to neutralize the translation of the so-produced sterility RNA. Examples of such antisense DNAs are the antisense DNAs of the sterility DNAs encoding the following second proteins: barnase; EcoRI; enzymes which catalyze the synthesis of phytohormones, such as isopentenyl transferase which is an enzyme that catalyzes the first step in cytokinin biosynthesis and is encoded by gene 4 of Agrobacterium T-DNA; enzymes involved in the synthesis of auxin and encoded by gene 1 and gene 2 of Agrobacterium T-DNA or alternatively the enzyme encoded by either gene 1 or gene 2; glucanases; lipases such as phospholipase $A_2$ (Verheij et al (1981) Rev. Biochem. Pharmacol. 91, 92–203); lipid peroxidases; plant cell wall inhibitors; and proteins toxic to plants cells, such as a bacterial toxin (e.g., the A-fragment of diphtheria toxin or botulin); as well as the antisense DNAs- of the sterility DNAs encoding natural self-incompatibility genes.

Further examples of fertility-restorer DNAs encode specific RNA enzymes (i.e., so-called "ribozymes"), capable of highly specific cleavage against a given target sequence as described by Haseloff and Gerlach (1988) Nature 334, 585–591. Such a ribozyme is, for example, the ribozyme targeted against one of the sterility DNAs cited above.

Still further examples of fertility-restorer DNAs can be combinations of one or more of the different fertility-restorer DNAs cited above.

By "foreign" with regard to the foreign DNA sequence of this invention is meant that the foreign DNA sequence contains a foreign fertility-restorer DNA and/or a foreign first promoter. By "foreign" with regard to a DNA, such as a fertility-restorer DNA and a first promoter, as well as a first marker DNA, a second promoter and any other DNA in the foreign DNA sequence, is meant that such a DNA is not in the same genomic environment in a plant cell, transformed with such a DNA in accordance with this invention, as is such a DNA when it is naturally found in the cell of the plant, bacteria, animal, fungus, virus, or the like, from which such a DNA originates. This means, for example, that a foreign fertility-restorer DNA or first marker DNA can be: 1) a nuclear DNA in a plant of origin; 2) endogenous to the transformed plant cell (i.e., from a plant of origin with the same genotype as the plant being transformed); and 3) within the same transcriptional unit as its own endogenous promoter and 3' end transcription regulation signals (from the plant of origin) in the foreign DNA sequence of this invention in the transformed plant cell; but 4) inserted in a different place in the nuclear genome of the transformed plant cell than it was in the plant of origin so that it is not surrounded in the transformed plant cell by the genes which surrounded it naturally in the plant of origin. A foreign fertility-restorer or first marker DNA can also, for example, be: 1) a nuclear DNA in a plant of origin; and 2) endogenous to the transformed plant cell; but 3) in the same transcriptional unit as a different (i.e., not its own) endogenous promoter and/or 3' end transcription regulation signals in a foreign chimaeric DNA sequence of this invention in a transformed plant cell. A foreign fertility-restorer or first marker DNA can also, for example, be: 1) a nuclear DNA in a plant of origin; and 2) endogenous to the transformed plant cell; but 3) in the same transcriptional unit as a heterologous promoter and/or 3' end transcription regulation signals in a foreign chimaeric DNA sequence of this invention in a transformed plant cell. A foreign fertility-restorer or first marker DNA can also, for example, be heterologous to the transformed plant cell and in the same transcriptional unit as an endogenous promoter and/or 3' transcription regulation signals (e.g., from the nuclear genome of a plant with the same genotype as the plant being transformed) in a foreign chimaeric DNA sequence of this invention in a transformed plant cell. An example of a foreign fertility-restorer DNA could come from the nuclear genome of a plant with the same genotype as the plant being transformed and encode an inhibitor of a catalytic enzyme, such as a protease or ribonuclease inhibitor, that is endogenous to the plant being transformed, so that the enzyme is overproduced in transformed cells in order to neutralize the activity of a protease or ribonuclease (i.e., a second protein encoded by a male- or female-sterility DNA) which would significantly disturb adversely the metabolism, functioning and/or development of flower cells, particularly male or female organ cells, or seed cells or embryo cells, in which such an enzyme is expressed. Preferably, each fertility-restorer DNA and first marker DNA is heterologous to the plant cell being transformed.

By "heterologous" with regard to a DNA, such as a fertility-restorer DNA, a first or third promoter, a first marker DNA and any other DNA in the foreign DNA sequence of this invention, is meant that such a DNA is not naturally found in the nuclear genome of cells of a plant with the same genotype as the plant being transformed. Examples of heterologous DNAs include chloroplast and mitochondrial DNAs obtained from a plant with the same genotype as the plant being transformed, but preferred examples are chloroplast, mitochondrial, and nuclear DNAs from plants having a different genotype than the plant being transformed, DNAs from animal and bacterial genomes, and chromosomal and plasmidial DNAs from fungal and viral genomes.

By "chimaeric" with regard to the foreign DNA sequence of this invention is meant that at least one of its fertility-restorer DNAs: 1) is not naturally found under the control of its first promoter for the one fertility-restorer DNA; and/or 2) is not naturally found in the same genetic locus as at least one of its first marker DNAs. Examples of foreign chimaeric DNA sequences of this invention comprise: a fertility-restorer DNA of bacterial origin under the control of a first promoter of plant origin; and a fertility-restorer DNA of plant origin under the control of a first promoter of plant origin and in the same genetic locus as a first marker DNA of bacterial origin.

By "flower" is meant to include the entire shoot axis, sepals, petals, male reproductive organs (or stamens) and/or female reproductive organs (or carpels) whose wholly or partly, retarded or arrested development would prevent the development and/or propagation of viable seeds in the flower or the development and/or propagation of its male gametes; by "male organ" or "male reproductive organ" is meant the entire organ of a flower that is involved in the production of the male gamete, as well as one or more of its individual parts such as its anther, pollen and filament; and by "female organ" or "female reproductive organ" is meant the entire organ of a flower that is involved in the production of the female gamete and/or viable seeds and/or viable embryos, as well as one or more of its individual parts such as its ovary, ovule, style, stigma, corolla, disc, septum, callyx and placenta. By "embryo", is meant to include the entire embryo of a plant, as well as one or more of its individual parts such as its embyo axis and embryo cotyledons.

So that the fertility-restorer DNA is expressed in at least those specific cells of a fertility-restored plant in which the sterility DNA is expressed, it is preferred that the first promoter, which controls expression of the fertility-restorer DNA, be a promoter capable of directing gene expression in at least the same fertility-restored plant cells (i.e., the specific flower cells, preferably male or female organ cells, or seed cells or embryo cells), in which the sterility DNA is selectively expressed under the control of the sterility promoter. Such a first promoter can be an endogenous promoter or an exogenous promoter and can be from the nuclear genome or from the mitochondrial or chloroplast genome of a plant cell. In any event, the first promoter is foreign to the nuclear genome of the plant cell being transformed. The first promoter can be a constitutive promoter but can also be the same selective promoter as the sterility promoter. Preferably, the first promoter causes the restoration of fertility through the production of at least sufficient amounts of fertility-restoring first RNA, protein or polypeptide selectively in the same specific flower, seed or embryo cells, particularly in the same specific flower cells, as those in which the sterility DNA is expressed.

The first promoter of this invention can be selected and isolated in a known manner from a plant species, for example as described in: U.S. Pat. No. 5,652,354 which is incorporated herein by reference and which discloses a male-sterility promoter that directs expression of a sterility DNA selectively in stamen (e.g., anther) cells of a plant and is effective to prevent expression of the sterility DNA in other parts of the plant; and U.S. Pat. No. 5,633,441 which is also incorporated herein by reference and which discloses a female-sterility promoter that directs expression of a sterility DNA selectively in cells of flowers, particularly cells of a female organ (e.g., pistil), or seed cells or embryo cells of a plant and is effective to prevent expression of the sterility DNA in other parts of the plant. For example, a suitable endogenous organ or tissue-specific first promoter can be identified and isolated in a plant, by:

1. searching for an mRNA which is only present in the plant during the development of its flowers, seeds or embryos, preferably its anthers, pollen, filaments, ovary, ovule, style, stigma, placenta, calyx, scutellum, septum, seedcoat, endosperm or embryo cotyledons;
2. isolating this specific mRNA;
3. preparing a cDNA from this specific mRNA;
4. using this cDNA as a probe to identify the regions in the plant genome which contain DNA coding for the specific mRNA; and then
5. identifying the portion of the plant genome that is upstream (i.e., 5') from the DNA coding for the specific mRNA and that contains the promoter of this DNA.

The genes controlled by these first promoters can further be used as probes as in step 4, above. Under hybridizing conditions, such a probe will hybridize to DNA coding for a specific mRNA in a mixture of DNA sequences from the genome of another plant species (Maniatis et al (1982) *Molecular Cloning. A Laboratory Manual.* Ed. Cold Spring Harbor Laboratory). Thereafter, as in step 5 above, a specific first promoter for another plant species can be identified.

Examples of male organ-specific first promoters and sterility promoters are: the PTA29 promoter, the PTA26 promoter and the PTA13 promoter, as described in U.S. Pat. No. 5,652,354, which have been isolated from tobacco and are tapetum-specific promoters; as well as any promoter of a gene encoding a tapetum-specific mRNA hybridizable to the genes TA29, TA26 or TA13 of U.S. Pat. No. 5,652,354, from which genes the PTA29, PTA26 and PTA13 promoters have been isolated. Examples of female organ-specific first promoters and sterility promoters are: the style and/or stigma-specific promoters, such as PSTMG07, PSTMG08, PSTMG4B12 and PSTMG3C9, and the ovule-specific promoter corresponding to the cDNA clone pMON9608 as described in U.S. Pat. No. 5,633,441; as well as a promoter of a gene encoding i) a style-stigma specific or ii) an ovule-specific mRNA hybridizable respectively to i) a STMG-type style-stigma specific gene or ii) CDNA clone pMON9608 of U.S. Pat. No. 5,633,441.

If more than one nuclear sterility DNA is present in the transgenic sterile plant which is to be crossed with the transgenic fertility-restorer plant of this invention, the restorer plant may need to have inserted into its nuclear genome more than one fertility-restorer DNA of this invention, corresponding in number at least to the number of sterility DNAs in the nuclear genome of the sterile plant. All the fertility-restorer DNAs can be under the control of a single first promoter, but preferably, each fertility-restorer DNA is under the control of its own separate first promoter, which will direct expression of the first RNA, protein or polypeptide at least in those cells where the sterility promoters cause the sterility DNAs to express the second RNA, protein or polypeptide. Each fertility-restorer DNA is adjacent to its first promoter, and all the fertility-restorer DNA(s) and their first promoter(s) are preferably adjacent to one another in the foreign DNA sequences of this invention and in any vectors used to transform plant cells with such foreign DNA sequences. However, it is not necessary that the fertility-restorer DNAs be adjacent to one another in the foreign DNA sequence, and in some cases, they may be inserted into the nuclear genome of the restorer plant through independent transformation events.

The selection of the first marker DNA of this invention also is not critical. A suitable first marker DNA can be selected and isolated in a well known manner, so that it encodes the third RNA, protein or polypeptide that allows plants, expressing the first marker DNA, to be easily distinguished and separated from plants not expressing the first marker DNA. In many cases, the first marker DNA encodes the same RNA, protein or polypeptide as the second marker DNA encodes in the nuclear male- or female-sterile plant, the fertility of which is to be restored in accordance with this invention. Examples of the first marker DNAs are the marker DNAs in the nuclear genomes of the nuclear male- and female-sterile plants described in U.S. Pat. Nos. 5,652,354 and 5,633,441 which encode proteins or polypeptides that: provide a distinguishable color to plant cells, such as the A1 gene encoding dihydroquercetin-4-reductase (Meyer et al (1987) Nature 330, 677–678) and the glucuronidase gene (Jefferson et al (1988) Proc. Natl. Acad. Sci. USA ("PNAS") 83, 8447); provide a specific morphological characteristic to a plant such as dwarf growth or a different shape of the leaves; confer on a plant stress tolerance, such as is provided by the gene encoding superoxide dismutase as described in EP 359617; confer disease or pest resistance on a plant, such as is provided by a gene encoding a *Bacillus thuringiensis* endotoxin conferring insect resistance as described in European patent application 86300291.1 published on Sep. 3, 1986, as EP 0193259; or confer on a plant a bacterial resistance such as is provided by the bacterial peptide described in European patent application 88401673.4 published on Jan. 18, 1989 as EP 0299828.

Preferred first marker DNAs encode third proteins or polypeptides inhibiting or neutralizing the activity of herbicides such as: the sfr gene and the sfrv gene encoding enzymes conferring resistance to glutamine synthetase inhibitors such as Bialaphos and phosphinotricine as described in European patent application 87400544.0 published Oct. 21, 1987, as EP 0242246; and genes encoding modified target enzymes for certain herbicides that have a lower affinity for the herbicides than naturally produced endogenous enzymes, such as a modified glutamine synthetase as a target for phosphinotricine as described in European potent publication 0,240,792 and a modified 5-enolpyruvylshikimate-3 phosphate synthase as a target for glyphosate as described in European patent publication 0,218,571. Other first marker DNAs encode third proteins which neutralize the action of the herbicide bromoxynil (Stalker et al (1988) in: Genetic Improvements of Agriculturally important Crops. Ed: R. T. Fraley, N. M. Frey and J. Schell. Cold Spring Harbor Laboratories) or the herbicide sulfonylurea (Lee et al (1988) EMBO J. 7, 1241–1248) or the herbicide 2,4 D (disclosed at the 2nd International Symposium of Plant Molecular Biology, Jerusalem, 13–18 November 1988).

The second promoter of this invention, which controls the first marker DNA, can also be selected and isolated in a well known manner so that the first marker DNA is expressed either selectively in one or more specific tissues or specific cells or constitutively in the entire plant, as desired depending on the nature of the third RNA, protein or polypeptide. In many cases, the second promoter is the same as the third promoter which controls the second marker DNA in the male- or female-sterile plant, the fertility of which is to be restored in accordance with this invention. For example, if the first marker DNA encodes an herbicide resistance, it may be useful to have the first marker DNA expressed in all cells of the plant, using a strong constitutive second promoter such as a 35S promoter (Odell et al (1985) Nature 313, 810–812), a 35S'3 promoter (Hull and Howell (1987) Virology 86, 482–493), the promoter of the nopaline synthetase gene ("PNOS") of the Ti-plasmid (Herrera-Estrella (1983) Nature 303, 209–213) or the promoter of the octopine synthase gene ("POCS"[De Greve et al (1982) J. Mol. Appl. Genet. 1 (6), 499–511]). If the first marker DNA encodes a protein conferring disease resistance, it may be useful to have the first marker DNA selectively expressed in wound tissue by using, for example, a second promoter which is a TR promoter such as the TR1' or TR2' promoter of the Ti-plasmid (Velten et al (1984) EMBO J. 3, 2723–2730). If the first marker DNA encodes a herbicide resistance, it may be useful to have the first marker DNA selectively expressed in green tissue by using as the second promoter, for example, the promoter of the gene encoding the small subunit of Rubisco (European patent application 87400544.0published Oct. 21, 1987, as EP 0242246). If the first marker DNA encodes a pigment, it may be useful to select the second promoter so that the first marker DNA is expressed in specific cells, such as petal cells, leaf cells or seed cells, preferably in the outer layer of the seed coat.

One can identify and isolate in a well known manner a tissue-specific second promoter, suitable for inclusion in the foreign DNA sequence of this invention in a restorer plant or a restored plant of this invention, whereby the plant can be easily distinguished as carrying the first marker DNA under the control of the second promoter. This can be done by:

1. searching for an mRNA which is only present in the plant during the development of a specific tissue, such as its petals, leaves or seeds;
2. isolating this tissue-specific mRNA;
3. preparing a cDNA from this tissue-specific mRNA;
4. using this cDNA as a probe to identify the regions in the plant genome which contain DNA coding for the tissue-specific mRNA; and then
5. identifying the portion of the plant genome that is upstream from the DNA coding for the tissue-specific mRNA and that contains the promoter for said DNA.

If more than one first marker DNA is present in the foreign DNA sequence of this invention, all the first marker DNAs can be under the control of a single second promoter, but preferably, each first marker DNA is under the control of its own separate second promoter. More preferably, each first marker DNA is under the control of its own second promoter and encodes a different third RNA, protein or polypeptide, providing different distinguishable characteristics to a transformed plant. In any event, the first marker DNA(s) and second promoter(s) should be adjacent to each other and to the one or more fertility-restorer DNAs contained in the foreign DNA sequence of this invention and in any vector used to transform plant cells with the foreign DNA sequence.

It is generally preferred that the first RNA, protein or polypeptide, encoded by the fertility-restorer DNA, substantially prevent the activity of the second RNA, protein or polypeptide, encoded by the sterility DNA, in the cytoplasm or the nucleus of the plant cells in which the sterility DNA is expressed. However, when it is desired to have the first protein or polypeptide and/or the third protein or polypeptide transported from the cytoplasm into chloroplasts or mitochondria of the cells of transformed plants, the foreign DNA sequence can further include an additional foreign DNA encoding a transit peptide. The additional DNA is between the fertility-restorer DNA and the first promoter if the first protein or polypeptide is to be so-transported and is between the first marker DNA and the second promoter if the third protein or polypeptide is to be so-transported. By "transit peptide" is meant a polypeptide fragment which is normally associated with a chloroplast or mitochondrial protein or subunit of the protein and is produced in a cell as a precursor protein encoded by the nuclear DNA of the cell. The transit peptide is responsible for the translocation process of the nuclear-encoded chloroplast or mitochondrial protein or subunit into the chloroplast or the mitochondria, and during such a process, the transit peptide is separated or proteolytically removed from the chloroplast or mitochondrial protein or subunit. One or more of such additional DNAs can be provided in the foreign DNA sequence of this invention for transporting one or more first or third proteins or polypeptides as generally described in European patent application 85402596.2 published on Aug. 6, 1986, as EP 0189707 and in: Van den Broeck et al (1985) Nature 313, 358–363; Schatz (1987) Eur. J. of Bioch. 165, 1–6; and Boutry et al (1987) Nature 328, 340–342. An example of a suitable transit peptide for transport into chloroplasts is the transit peptide of the small subunit of the enzyme RUBP carboxylase (European patent application 85402596.2published on Aug. 6, 1986, as EP 0189707) and an example of a transit peptide for transport into mitochondria is the transit peptide of the enzyme Mn-superoxide dismutase (U.S. Pat. No. 5,652,354; see also Example 3 herein).

In the foreign DNA sequence of this invention, 3' transcription termination signals can be selected from among those which are capable of providing correct transcription termination and polyadenylation of mRNA in plant cells. The transcription termination signals can be the natural ones of the foreign gene or DNA to be transcribed or can be foreign or heterologous. Examples of heterologous transcription termination signals are those of the octopine synthase gene (Gielen et al (1984) EMBO J. 3, 835–845) and the T-DNA gene7 (Velten and Schell (1985) Nucleic Acids Research ("NAR") 13, 6981–6998).

Also in accordance with this invention, a culture of plant cells, containing the foreign DNA sequence of this invention, can be used to regenerate homozygous dominant fertility-restorer plants by performing the necessary transformation: on a haploid cell culture (Chuong and Beversdof (1985) Plant Sci. 39, 219–226) and then doubling the number of chromosomes by well known techniques (e.g., by the use of colchicine); or alternatively, on a diploid cell culture and then culturing anthers of regenerated plants to produce haploid progeny which can afterwards be rendered diploid. See: Plant Tissue and Cell Culture, Plant Biology 3, A. R. Liss, Inc. N.Y. (1987). Thereby, the foreign DNA sequence will be in homozygous form in the nuclear genome of each of the so-transformed plant cells of the culture. This is preferred for a plant cell culture containing a fertility-restorer DNA under the control of a first promoter which directs gene expression at a given stage of development of: i) the plant's male gametes, such as pollen, especially after meiosis, ii) the plant's female gametes, such as ova, especially after meiosis, or iii) cells derived from the male or female gametes, such as seed or embryo cells, so that the fertility-restorer DNA is present and can be expressed in all male or female gametes or plant cells derived therefrom.

Further in accordance with this invention, processes are provided for producing hybrid seeds which can be grown into hybrid fertility-restored plants. One process involves crossing: a nuclear male-sterile female-fertile plant including at least one second marker DNA under the control of at least one third promoter; with a homozygous nuclear male-fertile restorer plant including at least one nuclear male fertility-restorer DNA under the control of at least one first promoter but without a first marker DNA that is the same as the second marker DNA. In this process, the male-sterile and male-fertile plants are sown at random, and after pollination, the selectable marker, encoded by the second marker DNA, is used to eliminate the fertility-restorer plants, ensuring that seed is only harvested on the male-sterile plants. This guarantees that all harvested seeds are both hybrid and fertile. Another process involves crossing: a nuclear male-sterile female-fertile restorer plant including a nuclear first marker DNA under the control of a second promoter and a nuclear female fertility-restorer DNA under the control of a first promoter in a homozygous form; with a nuclear male-fertile female-sterile restorer plant including at least the same nuclear first marker DNA under the control of a second promoter and a nuclear male fertility-restorer DNA under the control of a first promoter in a homozygous form. Both male-sterile and male-fertile parent plants can be grown in a substantially random population, thereby increasing the chances of cross-pollination, without the need for precise planting patterns, and using the characteristic encoded by the first marker DNA. 100% fertile hybrid seeds can be harvested. Preferably in both of these processes, the first marker DNA is under the control of a constitutive second promoter and encodes a third protein or polypeptide that renders the sterile plant resistant to a particular herbicide. The non-desirable genotypes can then be destroyed before cross-pollination, using the particular herbicide.

A process in accordance with this invention of crossing: 1) fertility-restorer plants which contain a fertility-restorer DNA stably integrated in their nuclear genome and transmissible throughout generations as a dominant allele in accordance with this invention, with 2) male- or female-sterile plants which contain a sterility DNA, preferably both a sterility DNA and a second marker DNA, stably integrated in their nuclear genome and transmissible throughout generations as dominant alleles in accordance with U.S. Pat. Nos. 5,652,354 and 5,633,441, provides an alternative to, and several advantages over, presently used systems for breeding and producing hybrid crops as described below:

1. For crops which do not easily cross-pollinate and for which the seed is the economic harvest and has low multiplication rates, such as cereals (e.g., wheat, barley and oats), rice, cotton, and many legumes (e.g., soybean and pea), the process of this invention offers the possibility to produce 100% hybrid fertile offspring, thereby guaranteeing high seed set and normal yield. An example of a typical strategy for producing hybrid plants, using as parent plants male-sterile and female-sterile parent plants and a restorer for their respective sterilities, may include the following steps (wherein "FH1" stands for female-sterility linked to herbicide resistance 1, "RF" stands for the restorer of the female-sterility, "M1H1" stands for male-sterility 1 linked to herbicide resistance 1, "M2H2" stands for male-sterility 2 linked to herbicide resistance 2, "RM1" stands for restorer of male-sterility 1, "A" stands for female parent lines, and "B" stands for male parent lines):

A. Development of the female parent plant A
1Aa) Transform plant A with a fertility-restorer DNA of this invention that encodes a first RNA, protein or polypeptide (which neutralizes specifically the expression product of the female-sterility DNA in the male parent) and is under the control of a first promoter which directs gene expression in at least the same cells as those in which the female-sterility DNA in the male plant is to be expressed. This gives rise to $A^{RF/rf}$.

1Ab) Self-pollinate $A^{RF/rf}$, giving rise to 25% $A^{RF/RF}$ plants.

1Ac) Transform $A^{RF/RF}$ with a chimaeric DNA sequence including a "male-sterility DNA 1" under the control of a male organ specific promoter and a marker DNA conferring resistance to a herbicide 1. This gives rise to the male-sterile plant $A^{RF/RF;M1H1/mh}$.

1Ad) Multiply the male-sterile plant by crossing: $A^{RF/RF;M1H1/mh} \times A^{RF/RF;mh/mh}$ giving an offspring consisting of: 50% $A^{RF/RF;M1H1/mh}$: male-sterile 1, resistant to herbicide 1 and 50% $A^{RF/RF;mh/mh}$: male fertile, herbicide sensitive. This mixture is sown in successive generations of upscaling of the female parent, and the herbicide 1 is used in alternate rows or blocks of rows to create pure female parent stocks. The rows or blocks of rows where the herbicide is not applied are used as pollen source. Only seed of the herbicide treated rows or blocks of rows is harvested to constitute the next generation.

B. Development of the male parent plant B

For the economic production of B, the female-sterile parent line requires the use of two different sterility DNAs. The first one is a female-sterility DNA under the control of a promoter which directs gene expression selectively in cells of the female organ of the plant and linked to a marker DNA conferring resistance to herbicide 1. The second one is a male-sterility DNA (different from male-sterility DNA 1 and called "male-sterility DNA 2"), under the control of a promoter which directs gene expression selectively in male organ cells of the plant and is linked to a second marker DNA conferring resistance to herbicide 2.

1Ba) Transform plant B with a foreign DNA sequence of this invention encoding a first RNA, protein or polypeptide which neutralizes specifically the activity of the male-sterility DNA 1 expressed in the female parent and is under the control of a first promoter which directs gene expression in at least the same male organ cells in which the male-sterility DNA 1 in the female parent plant is expressed. This gives rise to $B^{RM1/rm}$.

1Bb) Self-pollinate $B^{RM1/rm}$, giving rise to 25% $B^{RM1/RM1}$.

1Bc) (1) Transform $B^{RM1/RM1}$ with a chimaeric DNA sequence including the female-sterility DNA under the control of a promoter which directs gene expression selectively in cells of the female-organ of the plant and a marker DNA conferring resistance to herbicide 1. This gives rise to the female-sterile plant $B^{RM1/RM1;FH1/fh}$. (2) Transform $B^{RM1/RM1}$ with a chimaeric DNA sequence including the male-sterility DNA 2 under the control of a male organ-specific promoter and a marker DNA conferring herbicide resistance to herbicide 2. This gives rise to the male-sterile plant $B^{RM1/RM1;M2H2/mh}$.

1Bd) (1) Multiply the male-sterile plant of 1Bc)(2) by crossing:
$B^{RM1/RM1;M2H2/mh} \times B^{RM1/RM1;mh/mh}$
giving an offspring consisting of:
50% $B^{RM1/RM1;M2H2/mh}$: male-sterile, resistant to herbicide and 50% $B^{RM1/RM1;mh/mh}$ male fertile, herbicide sensitive.

(2) Multiply the female-sterile plant of 1Bc)(1) by crossing:
$B^{RM1/RM1;M2H2/mh;fh/fh} \times B^{RM1/RM1;mh/mh;FH1/fh}$ which are planted in separate rows, giving rise to the following genotypes in the male-sterile rows:
25% $B^{RM1/RM1;M2H2/mh;FH1/fh}$: sterile and resistant to herbicide 1 and 2,
25% $B^{RM1/RM1;mh/mh;FH1/fh}$ female-sterile and resistant to herbicide 1,
25% $B^{RM1/RM1;M2H2/mh;fh/fh}$: male-sterile and resistant to herbicide 2, and
25% $B^{RM1/RM1;mh/mh;fh/fh}$: fertile and herbicide sensitive.

1Be) This mixture can be used again as the male parent ($B^{RM1/RM1;mh/mh;FH1/fh}$) in further multiplication crosses, whereby spraying in each generation with herbicide 1 eliminates the female fertile plants and so maintains the male parent line. This mixture will be planted in alternate rows or blocks of rows with the mixture obtained in 1 Bd (1), which mixture will be treated with herbicide 2 to eliminate male fertile plants. Alternatively, the mixture obtained in 1 Bd) (2) can be sown as such and alternate rows can be treated either with herbicide 1 or either with herbicide 2. Under such circumstances, step 1 Bd)(1) is not necessary.

C. Production of hybrid seed AB

Sow at random the mixtures obtained in the steps 1Ad) and 1Be). Before cross-pollination occurs, spray with herbicide 1 in order to eliminate all undesirable genotypes. Cross pollination occurs with:
$A^{RF/RF;rm/rm;M1H1/mh;fh/fh} \times B^{RM1/RM1;rf/rf;mh/mh;FH1/fh}$,
giving rise to:
25% $AB^{RF/rf;M1H1/mh;rm/RM1;FH1/fh}$
25% $AB^{RF/rf;M1H1/mh;rm/RM1;fh/fh}$
25% $AB^{RF/rf;mh/mh;rm/RM1;FH1/fh}$
25% $AB^{RF/rf;mh/mh;rm/RM1;fh/fh}$
constituting 100% fertile hybrid seed.

2. Depending on the special characteristics of the crop which is bred, the foregoing general strategy can be simplified. Such special characteristics include:

(2.1) If the crop undergoes a reasonable or good cross-pollination by insects, the relative proportion of parent line B in the mixture can be lowered without affecting the yield of the crop (e.g., cotton, a legume such as Pisum, alfalfa, oilseed rape and corn). Alternatively, a much simplified breeding scheme can be used for a crop involving a female parent which has been rendered male-sterile and herbicide resistant and a male parent carrying the fertility-restorer gene for the male-sterility. This would permit the following strategy: Cross: $A^{MH/mh} \times B^{RM/RM}$ sown at random or in rows for crops which do not flower synchronously. Treat with herbicide after pollination when sown at random. Yielding: 50% $AB^{MH/mh;RM/rm}$ and 50% $AB^{mh/mh;RM/rm}$, constituting 100% fertile hybrid offspring.

(2.2) In case F2 offspring represent the commercial seed product (e.g. cotton), the following variant strategy can be used:

a) Produce by transformation male-sterile plants of parent line A, giving $A^{M/m;r/r}$;

b) Produce by 2 independent transformation events fertility-restorer plants carrying into two independent genetic loci of its nuclear genome the fertility-restorer gene the product of which neutralizes specifically the activity the male-sterility gene in the male-sterile plant of a) and obtain by self-pollination both restorer genes in a homozygous form, giving $B^{m/m;R1/R1;R2/R2}$;

c) Cross $A^{M/m;r/r} \times B^{m/m;R1/R1;R2/R2}$ yielding 50% $AB^{M/m;R1/r;R2/r}$ and 50% $AB^{m/m;R1/r;R2/r}$ constituting 100% hybrid fertile offspring; and d) Self-pollinate the mixture obtained in c). Half of the offspring are as shown in Table 1, below, only 1 of a total of 64 plants being male-sterile (indicated by an * in Table 1), and all the others being fertile.

This result makes this process economically valuable.

TABLE 1

| AB\AB | sR1R2 | sR1r2 | sr1R2 | sr1r2 |
|---|---|---|---|---|
| R1R2 | sR1R2/SR1R2 | sR1r2/SR1R2 | sr1R2/SR1R2 | sr1r2/SR1R2 |
| SR1r2 | sR1R2/Sr1R2 | sR1r2/SR1r2 | sr1R2/SR1r2 | sr1r2/SR1r2 |
| Sr1R2 | sR1R2/Sr1R2 | sR1r2/Sr1R2 | sr1R2/Sr1R2 | sr1r2/Sr1R2 |
| Sr1r2 | sR1R2/Sr1r2 | sR1r2/Sr1r2 | sr1R2/Sr1r2 | sr1r2/Sr1r2* |
| sR1R2 | sR1R2/SR1R2 | sR1r2/sR1R2 | sr1R2/sR1R2 | sr1r2/sR1R2 |
| sR1r2 | sR1R2/sR1r2 | sR1r2/sR1r2 | sr1R2/sR1r2 | sr1r2/sR1r2 |
| sr1R2 | sR1R2/sr1R2 | sR1r2/sr1R2 | sr1R2/sr1R2 | sr1r2/sr1R2 |
| sr1r2 | sR1R2/sr1r2 | sR1r2/sr1r2 | sr1R2/sr1r2 | sr1r2/sr1r2 |

(2.3) If the male-sterility DNA 2 is linked to another marker DNA than the one encoding resistance to herbicide 2, e.g. a color gene, the plants carrying this male-sterility DNA could be easily eliminated without damage to the other plants. Alternatively, the male-sterility DNA 2 could be introduced without any selectable marker DNA. Eliminating plants carrying the male-sterility DNA 2 could be done through manual selection, which needs only to be done on a small scale (See (1) Bd), above).

(2.4) If the tissue of the parent plants to be transformed is constituted of haploid material, this would reduce considerably the subsequent breeding, presenting the dominant genes encoding sterility in a homozygous form.

(2.5) If the value of the seed, or the cost of hand labor allows manual elimination of unwanted genotypes, at least up to the last stages before the hybrid production, the general system could also be simplified.

3. Another example of a breeding strategy—using male- and female-sterility combined with the fertility restorer system of this invention—may include the following steps:

3A. Development of the female parent line A

3Aa) Transform line A with a foreign DNA sequence including a fertility-restorer DNA of this invention which: encodes a first RNA, protein or polypeptide that neutralizes specifically the activity of the product of a female-sterility DNA expressed in the male parent; is under the control of a first promoter that directs expression of the fertility-restorer DNA in at least the same female organ cells as those in which the female-sterility DNA of the male parent is expressed; and is adjacent to a first marker DNA encoding resistance to herbicide 2. This gives rise to $A^{RFH2/rfh}$. Transform also, in parallel, line A with a DNA sequence including a male-sterility DNA which: is under the control of a male organ-specific promoter; and is adjacent to a second marker DNA encoding a different herbicide resistance (i.e., to herbicide 1) from the one encoded by the first marker DNA. This gives rise to $A^{MH1/mh}$ 3Ab) Cross $A^{RFH2/rfh} \times A^{MH1/mh}$, giving rise to 25% $A^{RFH2/rfh;MH1/mh}$
25% $A^{RFH2/rfh;mh/mh}$
25% $A^{rfh/rfh;MH1/mh}$
25% $A^{rfh/rfh;mh/mh}$.

Spray with herbicides 1 and 2, selecting $A^{RFH2/rfh;MH1/mh}$.

3Ac) Self-pollinate $A^{RFH2/rfh} \times A^{RFH2/rfh}$ giving rise to 25% $A^{RFH2/RFH2}$, which can be maintained by self-pollination.

3Ad) Cross $A^{RFH2/RFH2;mh/mh} \times A^{RFH2/rfh;MH1/mh}$.

This gives rise to:
25% $A^{RFH2/RFH2;MH1/mh}$
25% $A^{RFH2/RFH2;mh/mh}$
25% $A^{RFH2/rfh; MH1/mh}$
25% $A^{RFH2/rfh; mh/mh}$ whereby the male-sterile plants, having the fertility-restorer DNA in homozygous form, can be selected by spraying with herbicide 1 and by test-crossing with parental A line.

3Ae) Maintain the female parent line A by crossing: $A^{RFH2/RFH2;MH1/mh} \times A^{RFH2/RFH2;mh/mh}$.

B. Development of the male parent line B

3Ba) Transform line B with a foreign DNA sequence including a fertility-restorer DNA of this invention which: encodes a first RNA, protein or polypeptide that neutralizes specifically the activity of the product of a male-sterility DNA expressed in the female parent; is under the control of a first promoter that directs expression of the fertility-restorer DNA in at least the same male organ cells as those in which the male-sterility DNA is expressed; and is adjacent to a first marker DNA encoding resistance to herbicide 2. This gives rise to $B^{RMH2/rmh}$. Transform, in parallel, also line B with a DNA sequence including a female-sterility DNA which: is under the control of a female organ-specific promoter; and is adjacent to a second marker DNA encoding resistance to herbicide 1. This gives rise to $B^{FH1/fh}$.

Bb) Cross $B^{RMH2/rmh;fh/fh} \times B^{rmh/rmh;FH1/fh}$, giving rise to:
25% $B^{RMH2/rmh;FH1/fh}$
25% $B^{RMH2/rmh;fh/fh}$
25% $B^{rmh/rmh;FH1/fh}$
25% $B^{rmh/rmh; fh/fh}$ Isolate $B^{RMH2/rmh;FH1/fh}$ by spraying with herbicides 1 and 2.

3Bc) Self-pollinate $B^{RMH2/rmh} \times B^{RMH2/rmh}$ giving rise to:
25% $B^{RMH2/RMH2}$ which can be maintained through self-pollination.

3Bd) Cross $B^{RMH2/RMH2} \times B^{RMH2/rmh;FH1/fh}$ giving rise to:
25% $B^{RMH2/RMH2;fh/fh}$
25% $B^{RMH2/RMH2;FH/fh}$
25% $B^{RMH2/rmh;FH1/fh}$
25% $B^{RMH2/rmh;fh/fh}$ whereby the female-sterile plants having the fertility-restorer DNA in homozygous form are selected by spraying with herbicide 1 and by test-crossing with parental B line.

3Be) Maintain the male parent line B by crossing: $B^{RMH2/RMH2;fh/fh} \times B^{RMH2/RMH2;FH1/fh}$.

C. Alternative procedure for development of male or female parent plant (A or B are both designated by C)

3Ca) Transform line C with a foreign DNA sequence including a fertility-restorer DNA of this invention which: encodes a first RNA, protein or polypeptide

19 that neutralizes specifically the activity of the product of a sterility DNA expressed in the other parent; is under the control of a first promoter that directs expression of the fertility restorer DNA in at least the cells in which the sterility DNA of the other parent is expressed; and is adjacent to a first marker DNA encoding resistance to herbicide 2. This gives rise to $C^{RH2/rh}$.

3Cb) Self-pollinate $C^{RH2/rh} \times C^{RH2/rh}$, producing 25% $C^{RH2/RH2}$ which can be maintained through self-pollination.

3Cc) Transform $C^{RH2/RH2}$ with a DNA sequence including a sterility DNA which is: under the control of a male or female organ-specific promoter and adjacent to a second marker DNA encoding resistance to herbicide 1. This gives rise to $C^{RH2/RH2;SH1/sh}$ (wherein "S" stands for male- or female-sterility).

3Cd) Maintain line C by the following cross: $C^{RH2/RH2;SH1/sh} \times C^{RH2/RH2;sh/sh}$.

3D Production of hybrid seed AB Sow at random the mixtures obtained in steps 3Ae) and 3Be) or the mixture obtained in step 3Cd). Before cross-pollination occurs, spray with herbicides 1 and 2 in order to eliminate all undesirable genotypes. This leads to the following cross:
$A^{RFH2/RFH2;rm/rm;MH1/mh;fh/fh} \times_B RMH2/RMH2;rf/rf;FH1/fh;mh/mh}$.

This gives rise to the following offspring:
25% $AB^{RFH2/rf;RMH2/rm;MH1/mh;FH1/fh}$
25% $AB^{RFH2/rf;RMH2/rm;MH1/mh;fh/fh}$
25% $AB^{RFH2/rf;RMH2/rm;mh/mh;FH1/fh}$
25% $AB^{RFH2/rf;RMH2/rm;mh/mh;fh/fh}$ consisting of 100% hybrid fertile seed.

4. Other advantages of the fertility-restorer system of this invention, combined with the male- or female-sterility systems described in U.S. Pat. Nos. 5,652,354 and 5,633,441, compared to earlier systems, include:

a) A fool-proof production scheme, with several well distinguishable and selectable markers to control quality;

b) A considerable reduction in complexity at the level of the final seed multiplier, which is essential for reliable production and reduced production costs; and c) Reduction of the time necessary for the production of a commercial hybrid seed.

The following Examples illustrate the invention. Unless otherwise stated in the Examples, all procedures for making and manipulating recombinant DNA were carried out by the standardized procedures described in Maniatis et al, *Molecular Cloning—A Laboratory Manual*, Cold Spring Harbor Laboratory (1982). The following plasmids and vectors, used in the Examples, have been deposited in the Deutsche Sammlung Fur Mikroorganismen und Zellculturen ("DSM"), Mascheroder Weg 1B, D-3300 Braunschweig, Federal Republic of Germany under the provisions of the Budapest Treaty:

| Plasmid or vector | DSM Accession No. | Date |
| --- | --- | --- |
| PMB3 | 4470 | 21 Mar. 1988 |
| pGSC1700 | 4469 | 21 Mar. 1988 |
| pGV2260 | 2799 | Dec. 1983 |

EXAMPLE 1

Construction of a chimaeric DNA sequence of PTA29 and a barstar gene

A plasmid named "pTVE74", shown in FIG. 1, is constructed by assembling the following well known DNA fragments with the PTA29 promoter:

20

1. a vector fragment, including T-DNA border sequences, derived from pGSC1700 (Cornelissen and Vandewiele (1989) NAR 17 (1) 19–29) in which the β-lactamase gene has been deleted; located between the border sequences are the following DNA fragments 2 and 3;

2. a chimaeric sequence containing the promoter cassette PTA29 from U.S. Pat. No. 5,652,354, fused in frame at the ATG initiation codon with a *Bacillus amyloliquefaciens* gene encoding barstar, which is the cellular inhibitor of the extracellular ribonuclease, Barnase (Hartley et al (1972) Preparative Biochemistry 2 (3) 243–250; Hartley and Smeaton (1973) J. Biol. Chem. 248 (16), 5624–5626); the following steps are carried out:

a) The nucleotide sequence GCAC, at positions 7 to 10 up-stream of the first ATG codon, is mutated into nucleotide sequence ATCG, in order to obtain a suitable ClaI cloning site at the first methionine codon of the coding sequence (see FIG. 2); this is accomplished using site directed mutagenesis and yields pMc5-TPBSC; the ClaI protruding ends are digested by the enzyme, SI, and the barstar gene is isolated as a ClaI-HindIII fragment of 330 nucleotides (FIG. 2); and b) The SI-treated ClaI-HindIII fragment of pMc5-TPBSC is fused with the SI-treated NcoI-HindIII fragment of pMB3 (U.S. Pat. No. 5,652,354) and with a restriction fragment containing the 3' end signals of the nopaline synthetase ("NOS") gene for transcription termination and polyadenylation (An et al (1985) EMBO J. 4 (2), 277); and 3. a chimaeric sequence containing an *Arabidopsis Rubisco* SSU promoter ("PSSU" or "PSSUARA"), a neo gene encoding kanamycin resistance (European patent application 87400,544.0published on Oct. 21, 1987, as EP 0242246) and the 3' end signals of the octopine synthase ("OCS") gene (Dhaese et al (1983) EMBO J. 2, 419).

pTVE74 is a binary type T-DNA vector containing, within the T-DNA border sequences, three chimaeric sequences: PNOS-neo and PSSU-sfr which comprise first marker DNAs under the control of their own second promoters; and PTA29-barstar in which barstar is a fertility-restorer DNA whose expression under the control of the tapetum-specific PTA29 first promoter will neutralize, in tapetum cells of an otherwise male-sterile plant, the activity of Barnase encoded by a sterility DNA under the control of a tapetum-specific sterility promoter as described in U.S. Pat. No. 5,652,354.

EXAMPLE 2

Introduction of the chimaeric DNA sequence of Example 1 into tobacco and oilseed rape A recombinant Agrobacterium strain is constructed by mobilizing pTVE74 (from Example 1) from *E. coli* into *Agrobacterium tumefaciens* C58C1 Rif$^R$ containing pMP90 (Koncz and Schell (1986) Mol. Gen. Genetics 204, 383–396). The resulting Agrobacterium strain harboring pMP90 and pTVE74 is used to transform tobacco leaf discs (*N. tabacum* Petite Havane SR1) using standard procedures as described, for example, in European patent application 87400544.0 published on Oct. 21, 1987, as EP 0242246 and to transform oilseed rape (*Brassica napus*) according to the procedure of Lloyd et al (1986) Science 234, 464–466 and Klimaszewska et al (1985) Plant Cell Tissue Organ Culture 4, 183–197. Carbenicillin is used to kill the Agrobacterium strains after infection.

Transformed calli are selected on substrate containing 100 ug/ml kanamycin, and resistant calli are regenerated into plants. After induction of shoots and roots, the transformants are transferred to the greenhouse and grown until they flower. The flowers are examined, and they exhibit a fully natural morphology. Pollens of these flowers are used to pollinate the nuclear male-sterile tobacco and oilseed rape plants containing the Barnase gene as a sterility DNA, under the control of the tapetum cell-specific PTA29 sterility promoter, described in Example 13 of U.S. Pat. No. 5,652, 354. Offspring of these pollinated male-sterile plants are analyzed, and 75% of their flowers do not exhibit a male-sterility phenotype (i.e., absence of a normal tapetum layer in the stamens of their flowers).

EXAMPLE 3

Construction of chimaeric DNA sequences of PTA29 and a EcoRI methylase gene

Figure 3:
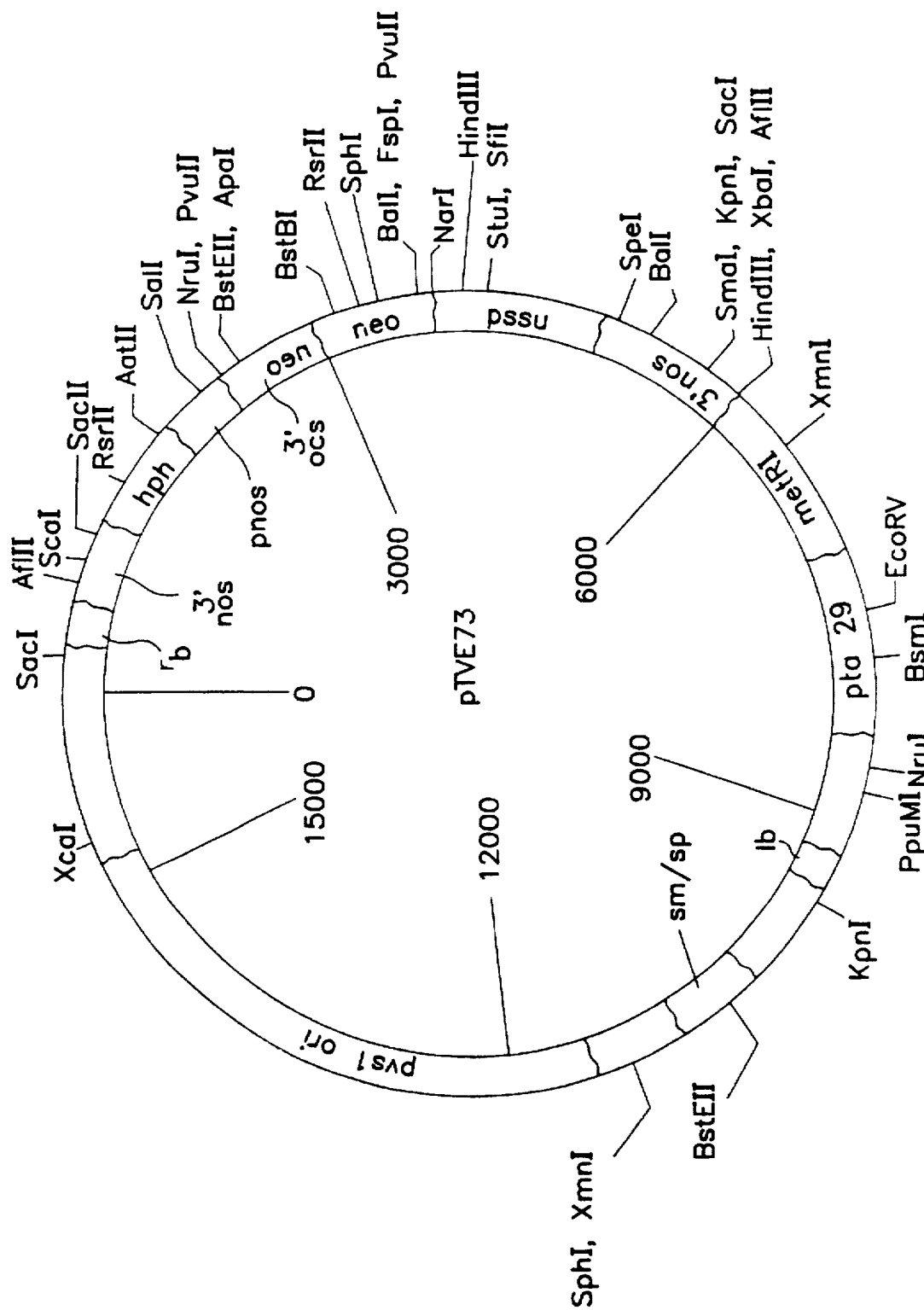
FIG. 3 shows a map of the vector pTVE73 of Example 3.

A plasmid named "pTVE73", shown in FIG. 3, is constructed by assembling the following well known fragments with the PTA29 promoter:

1. a vector fragment, including T-DNA border sequences, derived from pGSC1700 as described in Example 1 and with the following DNA fragments 2–4 between its border sequences;
2. the chimaeric sequence (no. 3) of Example 1, containing the pSSU promoter controlling expression of the neo gene and the 3' end of the OCS gene;
3. a chimaeric sequence, containing the nopaline-synthase promoter ("PNOS") [European patent application 87400544.0published on Oct. 21, 1987, as EP 0242246], the hph gene conferring resistance to hygromycine (Van den Elzen et al (1985) Plant Molecular Biology 5, 299–302) and the 3' end of the NOS gene (Example 1); and
4. a chimaeric sequence, containing the PTA29 promoter cassette from Example 1, fused in frame with the EcoRI methylase gene (Botterman and Zabeau (1985) Gene 37, 229–239), the expression product of which neutralizes the activity of the EcoRI restriction endonuclease—cleaving double stranded DNA at GAATTC sites (Wilson (1988) TIG 4 (11), 314–318); the following steps are carried out:
   a) a BglII-HindIII fragment from pEcoR4 (Botterman and Zabeau, 1985), containing the coding sequence of the EcoRI methylase, is cloned in pMa5–8 (EP 319353); by site directed mutagenesis a FspI site is introduced at the N-terminal of the methylase coding sequence
   TTA, ATG, GCT, AGA, AAT
          TGC, GCA
          FspI
   b) the promoter fragment of pMB3 is ligated at its filled NcoI site to the blunt FspI end, yielding PTA29
―――― c c <u>ATG, GCA</u>, . . .
       met RI .

and is fused with the 3' end of the NOS gene of Example 1.

pTVE73 is a binary type T-DNA vector containing, within the T-DNA border sequences, three chimaeric sequences; PSSU-neo and pNOS-hph which are first marker DNAs under the control of their own second promoters; and PTA29-EcoRI methylase gene which is a fertility-restorer DNA under the control of the tapetum-specific PTA29 first promoter. Expression in tapetum cells of an otherwise male-sterile plant of the fertility-restorer DNA under the control of the PTA29 promoter will neutralize the activity in such cells of EcoRI encoded by a sterility DNA under the control of a tapetum-specific sterility promoter as described in Example 16 of European patent application 89401134.9.

Figure 4:
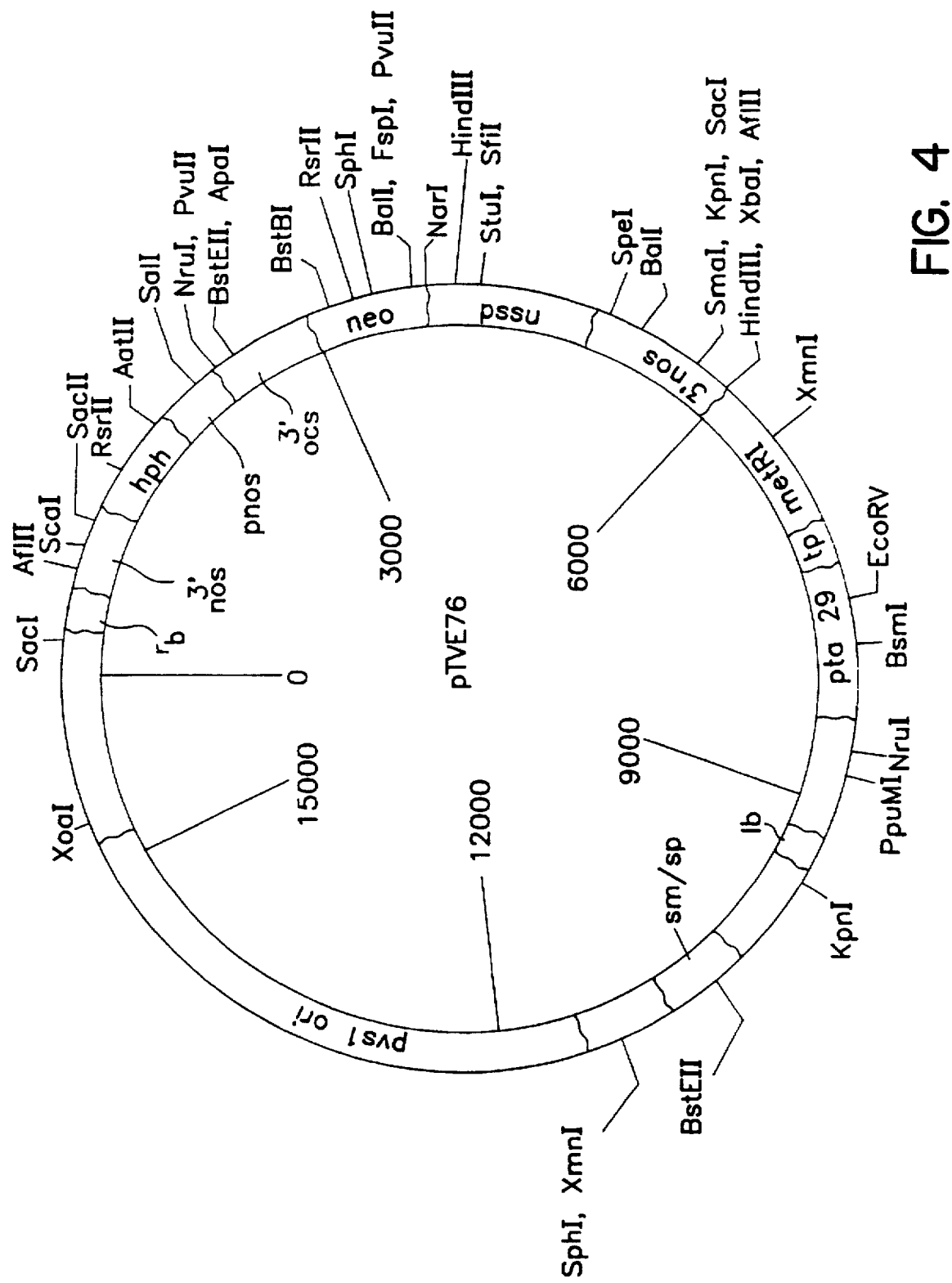
FIG. 4 shows a map of the vector pTVE76 of Example 3.

A plasmid named "pTVE76", shown in FIG. 4, is also constructed by assembling the following well known fragments with the PTA29 promoter:

1. A vector fragment, including T-DNA border sequences, derived from pGSC1700 (Cornelissen and Vandewiele (1989) NAR 17 (1) 19–29) in which the β-lactamase gene has been deleted and with the following DNA fragments 2–4 between its border sequences;
2. the chimaeric sequence (no. 3) of Example 1, containing the pSSU promoter, the neo gene and the 3' end of the OCS gene;
3. the chimaeric sequence, containing the PNOS promoter, the hph gene and the 3' end of the NOS gene; and
4. a chimaeric sequence containing the pTA29 promoter cassette from Example 1, fused in frame with a gene fragment encoding the transit peptide ("TP") of the Mn-superoxide dismutase ("Mn-SOD") (Bowler et al (1989) Embo J. 8, 31–38); the following modifications are made in the transit peptide sequence in order to isolate the fragment for cloning purposes using site directed mutagenesis as described in EP 319353:
   i. the AA nucleotides located upstream at position −2 and −1 of the ATG initiation codon are changed to CC nucleotides creating a NcoI site at the initiation codon and yielding the following nucleotide sequences:

― <u>CCATGG</u>CACTAC

NcoI ii the CTTG nucleotides located immediately at the processing site of the transit peptide are changed to GGTAC, creating a KpnI site at the processing site and yielding the following nucleotide sequences:

G   |  L   Q   T   F   S    L

CTC,CGC,GGC, | TTG,CAG,ACC,TTT,TCG,CTC

CTC,CGC,<u>GGG,</u> | <u>TAC</u>,CAG,ACC,TTT . . .
          ↓ KpnI in which the arrow indicates the processing site of the transit peptide sequence and the upper line indicates the aminoacid sequence corresponding with the Mn-SOD coding sequence; after treatment of the KpnI with Klenow DNA polymerase, the NcoI-KpnI fragment is fused in frame to the blunt FspI N-terminal of the EcoRI methylase coding sequence as used in the construction of pTVE73 and fused with the 3' end of the NOS gene of Example 1.

pTVE76 is a binary type T-DNA vector containing, within the T-DNA border sequences, three chimaeric sequences: PSSU-neo and PNOS-hph which first are marker DNAs under the control of their own second promoters; and PTA29-TP-EcoRI methylase gene which is a fertility-restorer DNA under the control of the PTA29 first promoter. Expression of EcoRI methylase, fused to the transit peptide of Mn-SOD, in tapetum cells of an otherwise male-sterile plant and targeting of the tapetum protein to the mitochondria of these cells will neutralize the activity in such cells ot EcoRI fused to a transit peptide and encoded by a corresponding sterility DNA under the control of a tapetum-specific promoter as described in Example 16 of U.S. Pat. No. 5,652,354.

EXAMPLE 4

Introduction of the chimaeric DNA sequences of Example 3 into tobacco and oilseed rape Recombinant Agrobacterium strains are constructed by mobilizing pTVE73 and pTVE76 of Example 3 from *E. coli* into Agrobacterium C58C1 Rif$^R$ containing pMP90 (Koncz and Schell (1986) Mol. Gen. Genetics 204, 383–396). The resulting strains, harboring respectively pMP90 and pTVE73 and pMP90 and pTVE76 are used for tobacco leaf disc transformation and for oilseed rape transformation as described in Example 2. Transformed calli and shoots are selected on substrates containing 100 ug/ml kanamycin.

The transformed shoots are rooted, transferred to soil in the greenhouse and grown until they flower. The flowers of both the tobacco and oilseed rape are examined, and both show a natural morphology. Pollen of these flowers is used to pollinate nuclear male-sterile tobacco and oilseed rape plants obtained by transformations with vectors pTVE63 and pTVE62, respectively (as described in Example 17 of U.S. Pat. No. 5,652,354), in which vectors the EcoRI gene is a sterility DNA under the control of a PTA29 sterility promoter and, in pTVE62, the EcoRI gene is also fused to DNA encoding the transit peptide of Mn-SOD. Offspring of these male-sterile plants are analyzed, and 75% of their flowers do not exhibit a male-sterility phenotype (i.e., absence of a normal tapetum layer in the stamens of their flowers).

Needless to say, this invention is not limited to the transformation of any specific plant(s). The invention relates to any plant, the nuclear genome of which can be transformed with a fertility-restorer DNA under the control of a first promoter that can direct expression of the fertility-restorer DNA selectively in at least cells of the plant's flowers, particularly at least one male or at least one female organ thereof, and/or seeds and/or embryos, whereby the plant can be both self-pollinated and cross-pollinated. For example, this invention relates to plants such as corn, oilseed rape, wheat, rice, sunflower, sugarbeet, tomato, lettuce, peppers, sorghum, soybean, pea, alfalfa, grasses, clovers, carrot, cabbages, leek, onion, tobacco, petunia, cacao and citrus trees.

Also, this invention is not limited to the specific plasmids and vectors described in the foregoing Examples, but rather encompasses any plasmids and vectors containing the fertility-restorer DNA under the control of the first promoter.

Furthermore, this invention is not limited to the specific first promoters described in the foregoing Examples, such as the PTA29 promoter, but rather encompasses any DNA sequence encoding a first promoter capable of directing expression of a fertility-restorer DNA at least in cells of a plant's flowers, seeds and/or embryos, where expression of a sterility DNA would otherwise cause the plant to be male- or female-sterile. In this regard, the first promoter of this invention encompasses: the promoters described in U.S. Pat. No. 5,652,354 for use in controlling the expression of a sterility DNA selectively in stamen cells of a plant to be rendered male-sterile; and the promoters described in U.S. Pat. No. 5,633,441 for use in controlling the expression of a sterility DNA selectively in cells of flowers, seeds or embryos of a plant to be rendered female-sterile. Alternatively, the first promoter can be a constitutive promoter for the plant, provided the first RNA, protein or polypeptide does not significantly disturb adversely the functioning, metabolism or development of cells in which it is expressed in the absence of expression of the sterility DNA.

In addition, this invention is not limited to the specific fertility-restorer DNAs described in the foregoing Examples but rather encompasses any DNA sequence encoding a first RNA, protein or polypeptide which, in a fertility-restored plant, neutralizes, blocks, offsets, overcomes or otherwise prevents the activity of the second RNA, protein or polypeptide that is encoded by the sterility-DNA under the control of the sterility promoter and that would otherwise significantly disturb adversely the metabolism, functioning and/or development of cells of flowers, seeds or embryos of the plant.

Also, this invention is not limited to the specific first marker DNAs described in the foregoing Examples but rather encompasses any DNA sequence encoding a third RNA, protein or polypeptide which confers on at least a specific plant tissue or specific plant cells, in which such DNA sequence is expressed, a distinctive trait compared to such a specific plant tissue or specific plant cells in which such DNA sequence is not expressed.

We claim:

1. A plant comprising a foreign DNA incorporated in the nuclear genome of its cells, said foreign DNA comprising a foreign restorer gene comprising:

(a) a fertility-restorer DNA encoding a restorer protein or polypeptide which neutralizes, blocks, offsets, overcomes or prevents the activity of a ribonuclease; and (b) a first promoter directing expression of said fertility-restorer DNA at least in specific stamen cells of said plant, said fertility restorer DNA being in the same transcriptional unit as, and under the control of, said first promoter; said plant being capable, when crossed to a male-sterile plant having a sterility DNA encoding said ribonuclease incorporated in its nuclear genome and selectively producing said ribonuclease in said specific stamen cells in order to kill or disable them, of producing male-fertile progeny comprising said sterility DNA and said fertility-restorer DNA.

2. The plant of claim 1, in which said foreign DNA further comprises:

(c) a marker DNA encoding a marker RNA, protein or polypeptide which, when present at least in a specific tissue or in at least specific cells of said plant, renders said plant separable from other plants which do not include said marker RNA, protein or polypeptide at least in said specific tissue or specific cells; and (d) a second promoter capable of directing expression of said marker DNA at least in said specific tissue or specific cells; said marker DNA being in the same transcriptional unit as, and under control of, said second promoter.

3. The plant of claim 2, wherein said foreign DNA further comprises:

(e) a DNA encoding a transit peptide capable of transporting said marker protein or polypeptide into a chloroplast or mitochondrion of at least said specific tissue or specific cells, said DNA being in the same transcriptional unit as said marker DNA and said second promoter and between said marker DNA and said second promoter.

4. The plant of claim 1, in which said restorer protein or polypeptide is barstar which comprises an amino acid sequence encoded by the barstar coding sequence as in FIG. 2 starting at position 11.

5. The plant of claim 1, in which said fertility-restorer DNA comprises the barstar coding sequence as in FIG. 2 starting at position 11.

6. The plant of claim 1, wherein said fertility restorer DNA is the ClaI-HindIII fragment of FIG. 2.

7. The plant of claim 1, wherein said first promoter is a promoter that directs expression selectively in stamen cells of said plant.

8. The plant of claim 1, wherein said first promoter is a promoter that directs expression selectively in anther cells.

9. The plant of claim 1, wherein said first promoter is a promoter that directs expression in tapetum cells, anther epidermal cells or tapetum and anther epidermal cells.

10. The plant of claim 1, wherein said promoter is PTA29, PTA13 or PTA26.

11. The plant of claim 2, wherein said marker DNA encodes a protein or polypeptide conferring a color to at least said specific tissue or specific cells; or encodes a protein or polypeptide conferring on said plant a stress tolerance, a disease or pest resistance or a bacterial resistance.

12. The plant of claim 11, wherein said marker encodes a *Bacillus thuringiensis* endotoxin that confers insect resistance, or encodes a bactericidal peptide that confers a bacterial resistance.

13. The plant of claim 2, wherein said marker DNA encodes a protein or polypeptide that inhibits or neutralizes herbicide activity.

14. The plant of claim 13, wherein said marker DNA encodes a modified target enzyme for an herbicide having lower affinity for the herbicide than an unmodified target enzyme.

15. The plant of claim 14, wherein said marker DNA encodes a protein or polypeptide which is a modified 5-enolpyruvylshikimate-3 phosphate synthase as a target for the herbicide glyphosate or a modified glutamine synthetase as a target for a glutamine synthetase inhibitor.

16. The plant of claim 13, wherein said marker DNA encodes a protein or polypeptide conferring resistance to a glutamine synthetase inhibitor.

17. The plant of claim 16, wherein said marker DNA is an sfr or sfrv gene.

18. The plant of claim 1, wherein said plant is corn, oilseed rape, wheat, rice, sunflower, sugarbeet, tomato, lettuce, peppers, sorghum, soybean, pea, alfalfa, grasses, clovers, carrot, cabbages, leek, onion, tobacco, petunia, cacao or citrus.

19. The plant of claim 2, wherein said second promoter is a constitutive promoter, a wound-inducible promoter, a promoter which directs expression selectively in plant tissue having photosynthetic activity, or a promoter which directs gene expression selectively in leaf cells, petal cells or seed cells.

20. The plant of claim 19, wherein said second promoter is a 35S promoter, a 35S'3 promoter, a promoter of a nopaline synthase gene, a TR1' or TR2' promoter, or a SSU promoter.

21. A vector suitable for transforming a cell of a plant which vector comprises the foreign restorer gene of claim 1.

22. A cell of a plant which comprises the foreign restorer gene of claim 1.

23. A seed of a plant which comprises the foreign restorer gene of claim 1.

24. A plant comprising a first foreign DNA and a second foreign DNA incorporated in the nuclear genome of its cells wherein said first foreign DNA comprises a sterility gene comprising:
 a sterility DNA encoding a ribonuclease which, when produced in stamen cells of said plant, is capable of killing or disabling them, and
 a sterility promoter capable of directing expression of said sterility DNA selectively in specific stamen cells of said plant, said sterility DNA being in the same transcriptional unit as, and under the control of, said sterility promoter; and wherein said second foreign DNA comprises a restorer gene comprising:
 a fertility-restorer DNA encoding a restorer protein or polypeptide which neutralizes, blocks, offsets, overcomes or prevents the activity of said ribonuclease; and
 a first promoter directing expression of said fertility-restorer DNA at least in said specific stamen cells of said plant, said fertility restorer DNA being in the same transcriptional unit as, and under control of, said first promoter; wherein said plant is male fertile due to the prevention of activity of said ribonuclease in said specific stamen cells by said restorer protein or polypeptide produced by expression of said fertility-restorer DNA at least in said specific stamen cells.

25. The plant of claim 24, in which said first foreign DNA and/or said second foreign DNA further comprises:
 (c) a marker DNA encoding a marker RNA, protein or polypeptide which, when present at least in a specific tissue or in at least specific cells of said plant, renders said plant separable from other plants which do not include said marker RNA, protein or polypeptide at least in said specific tissue or specific cells; and
 (d) a second promoter capable of directing expression of said marker DNA at least in said specific tissue or specific cells; said marker DNA being in the same transcriptional unit as, and under control of, said second promoter.

26. The plant of claim 25, wherein said first foreign DNA and/or said second foreign DNA further comprises:
 (e) a DNA encoding a transit peptide capable of transporting said marker protein or polypeptide into a chloroplast or mitochondrion of at least said specific tissue or specific cells, said DNA being in the same transcriptional unit as said marker DNA and said second promoter and between said marker DNA and said second promoter.

27. The plant of claim 24, wherein said restorer protein or polypeptide is barstar or a variant thereof which neutralizes, blocks, offsets, overcomes or prevents the activity of barnase.

28. The plant of claim 24, wherein said sterility promoter and said first promoter are promoters that direct expression selectively in anther cells of said plant.

29. The plant of claim 24, wherein said sterility promoter and said first promoter are identical.

30. The plant of claim 24, wherein said sterility promoter and said first promoter are promoters that direct expression in anther cells.

31. The plant of claim 24, wherein said sterility promoter and said first promoter are promoters that direct expression in tapetum cells, anther epidermal cells or tapetum and anther epidermal cells.

32. The plant of claim 24, wherein said sterility promoter and said first promoter are PTA29, PTA13 or PTA26.

33. The plant of claim 25, wherein said marker DNA encodes a protein or polypeptide conferring a color to at least said specific tissue or specific cells; or encodes a protein or polypeptide conferring on said plant a stress tolerance, a disease or pest resistance or a bacterial resistance.

34. The plant of claim 25, wherein said marker DNA encodes a *Bacillus thuringiensis* endotoxin that confers insect resistance, or encodes a bactericidal peptide that confers a bacterial resistance.

35. The plant of claim 25, wherein said marker DNA encodes a protein or polypeptide that inhibits or neutralizes activity of an herbicide.

36. The plant of claim 35, wherein said marker DNA encodes a modified target enzyme for an herbicide having lower affinity for the herbicide than an unmodified target enzyme.

37. The plant of claim 36, wherein said marker DNA encodes a protein or polypeptide which is a modified 5-enolpyruvylshikimate-3 phosphate synthase as a target for the herbicide glyphosate or a modified glutamine synthetase as a target for a glutamine synthetase inhibitor.

38. The plant of claim 35, wherein said marker DNA encodes a protein or polypeptide conferring resistance to a glutamine synthetase inhibitor.

39. The plant of claim 38, wherein said marker DNA is an sfr or sfrv gene.

40. The plant of claim 24, wherein said plant is corn, oilseed rape, wheat, rice, sunflower, sugarbeet, tomato, lettuce, peppers, sorghum, soybean, pea, alfalfa, grasses, clovers, carrot, cabbages, leek, onion, tobacco, petunia, cacao or citrus.

41. The plant of claim 25, wherein said second promoter is a constitutive promoter, a wound-inducible promoter, a promoter which directs expression selectively in plant tissue having photosynthetic activity, or a promoter which directs gene expression selectively in leaf cells, petal cells or seed cells.

42. The plant of claim 41, wherein said second promoter is a 35S promoter, a 35S'3 promoter, a promoter of a nopaline synthase gene, a TR1' or TR2' promoter, or a SSU promoter.

43. A cell of a plant which comprises a first foreign DNA and the second foreign DNA of claim 24.

44. A seed of a plant which comprises the first foreign DNA and the second foreign DNA of claim 24.

45. A system for breeding and producing hybrid crops, said system comprising:
(a) a male-sterile plant comprising a first foreign DNA incorporated in the nuclear genome of its cells which comprises a sterility gene comprising:
a sterility DNA encoding a ribonuclease which, when produced in stamen cells of said plant, is capable of killing or disabling them; and
a sterility promoter capable of directing expression of said sterility DNA selectively in specific stamen cells of said plant, said sterility DNA being in the same transcriptional unit as, and under the control of, said sterility promoter; and
(b) a male-fertile plant comprising a second foreign DNA incorporated in the nuclear genome of its cells which comprises a restorer gene comprising:
a fertility-restorer DNA encoding a restorer protein or polypeptide which neutralizes, blocks, offsets, overcomes or prevents activity of said ribonuclease; and
a first promoter directing expression of said fertility-restorer DNA at least in said specific stamen cells of said plant, said fertility restorer DNA being in the same transcriptional unit as, and under the control of, said first promoter; wherein said male-sterile and male-fertile plant can be crossed to produce male-fertile progeny comprising said first foreign DNA and said second foreign DNA.

46. The system of claim 45, in which said first foreign DNA and/or said second foreign DNA further comprises:
(c) a marker DNA encoding a marker RNA, protein or polypeptide which, when present at least in a specific tissue or in at least specific cells of said plant, renders said plant separable from other plants which do not include said marker RNA, protein or polypeptide at least in said specific tissue or specific cells; and
(d) a second promoter capable of directing expression of said marker DNA at least in said specific tissue or specific cells; said marker DNA being in the same transcriptional unit as, and under control of, said second promoter.

47. The system of claim 45, wherein said restorer protein or polypeptide is barstar or a variant thereof which neutralizes, blocks, offsets, overcomes or prevents the activity of barnase.

48. The system of claim 45, wherein said sterility promoter and said first promoter are promoters that direct expression selectively in anther cells of said plant.

49. The system of claim 45, wherein said sterility promoter and said first promoter are identical.

50. The system of claim 45, wherein said sterility promoter and said first promoter are promoters that direct expression in anther cells.

51. The system of claim 45, wherein said sterility promoter and said first promoter are promoters that direct expression in tapetum cells, anther epidermal cells or tapetum and anther epidermal cells.

52. The system of claim 45, wherein said sterility promoter and said first promoter are PTA29, PTA13 or PTA26.

53. The system of claim 46, wherein said marker DNA encodes a protein or polypeptide that inhibits or neutralizes activity of an herbicide, or encodes a protein or polypeptide conferring a color to said specific tissue or specific cells.

54. The system of claim 53, wherein said marker DNA encodes a protein or polypeptide conferring resistance to a glutamine synthetase inhibitor.

55. The system of claim 54, wherein said marker DNA is an sfr or sfrv gene.

56. The system of claim 46, wherein said second promoter is a constitutive promoter, a promoter which directs expression selectively in plant tissue having photosynthetic activity, or a promoter which directs gene expression selectively in seed cells.

57. The system of claim 56, wherein said second promoter is a 35S promoter, a 35S'3 promoter, a promoter of a nopaline synthase gene, or a SSU promoter.

58. A process for producing a seed, capable of growing into a fertility-restored plant comprising the steps of:
(a) crossing
(i) a male-sterile plant comprising a first foreign DNA incorporated in the nuclear genome of its cells which comprises a sterility gene comprising:
a sterility DNA encoding a ribonuclease which, when produced in stamen cells of said plant, is capable of killing or disabling them; and
a sterility promoter capable of directing expression of said sterility DNA selectively in specific stamen cells of said plant, said sterility DNA being in the same transcriptional unit as, and under the control of, said sterility promoter; and (ii) a male-fertile restorer plant comprising a second foreign DNA incorporated in the nuclear genome of its cells which comprises a restorer gene comprising:

a fertility-restorer DNA encoding a restorer protein or polypeptide which neutralizes, blocks, offsets, overcomes or prevents the activity of said ribonuclease; and a first promoter directing expression of said fertility-restorer DNA at least in said specific stamen cells of said plant, said fertility restorer DNA being in the same transcriptional unit as, and under the control of, said first promoter; and (b) obtaining seeds from said male-sterile plant that comprise said first foreign DNA and said second foreign DNA.

59. The process of claim 58, in which the seed is a hybrid seed.

60. The process of claim 58, in which said first foreign DNA and/or said second foreign DNA further comprises:

a marker DNA encoding a marker RNA, protein or polypeptide which, when present at least in a specific tissue or in at least specific cells of said plant, renders said plant separable from other plants which do not include said marker RNA, protein or polypeptide at least in said specific tissue or specific cells; and a second promoter capable of directing expression of said marker DNA at least in said specific tissue or specific cells; said marker DNA being in the same transcriptional unit as, and under control of, said second promoter.

61. The process of claim 58, wherein said restorer protein or polypeptide is barstar or a variant thereof which neutralizes, blocks, offsets, overcomes or prevents the activity of barnase.

62. The process of claim 58, wherein said sterility promoter and said first promoter are promoters that direct expression selectively in anther cells of said plant.

63. The process of claim 58, wherein said sterility promoter and said first promoter are identical.

64. The process of claim 58, wherein said sterility promoter and said first promoter and promoters that direct expression in anther cells.

65. The process of claim 58, wherein said sterility promoter and said first promoter are promoters that direct expression in tapetum cells, anther epidermal cells or tapetum and anther epidermal cells.

66. The process of claim 58, wherein said sterility promoter and said first promoter are PTA29, PTA13 or PTA26.

67. The process of claim 60, wherein said marker DNA encodes a protein or polypeptide that inhibits or neutralizes activity of an herbicide, or encodes a protein or polypeptide conferring a color to said specific tissue or specific cells.

68. The process of claim 67, wherein said marker DNA encodes a protein or polypeptide conferring resistance to a glutamine synthetase inhibitor.

69. The process of claim 68, wherein said marker DNA is an sfr or sfrv gene.

70. The process of claim 60, wherein said second promoter is a constitutive promoter, a promoter which directs expression selectively in plant tissue having photosynthetic activity, or a promoter which directs gene expression selectively in seed cells.

71. The process of claim 70, wherein said second promoter is a 35S promoter, a 35S'3 promoter, a promoter of a nopaline synthase gene, or a SSU promoter.

72. The plant of claim 15, wherein said glutamine synthetase inhibitor is phosphinothricin.

73. The plant of claim 16, wherein said marker DNA encodes a protein or polypeptide conferring resistance to phosphinothricin.

74. The plant of claim 38, wherein said marker DNA encodes a protein or polypeptide conferring resistance to phosphinothricin.

75. The system of claim 54, wherein said marker DNA encodes a protein or polypeptide conferring resistance to phosphinothricin.

76. The plant of claim 8, wherein said first promoter is a promoter that directs expression in tapetum cells.

77. The plant of claim 28, wherein said first promoter is a promoter that directs expression in tapetum cells.

78. The system of claim 48, wherein said first promoter is a promoter that directs expression in tapetum cells.

79. The process of claim 62, wherein said first promoter is a promoter that directs expression in tapetum cells.

80. A chimeric gene comprising:

(a) a DNA encoding a protein or polypeptide which neutralizes, blocks, offsets, overcomes or prevents the activity of a ribonuclease; and (b) a promoter directing expression of said DNA at least in specific stamen cells in a plant, said DNA being in the same transcriptional unit as, and under the control of, said promoter.

81. The chimeric gene of claim 80, in which said protein or polypeptide is barstar or a variant thereof which neutralizes, blocks, offsets, overcomes or prevents the activity of barnase.

82. The chimeric gene of claim 81, in which said barstar is encoded by the barstar coding sequence as in FIG. 2 starting at position 11.

83. The chimeric gene of claim 80, in which said DNA comprises the barstar coding sequence as in FIG. 2 starting at position 11.

84. The chimeric gene of claim 80, wherein said restorer DNA is the ClaI-HindIII fragment of FIG. 2.

85. The chimeric gene of claim 80, wherein said promoter is a promoter that directs expression selectively in stamen cells of said plant.

86. The chimeric gene of claim 80, wherein said promoter is a promoter that directs expression selectively in anther cells.

87. The chimeric gene of claim 80, wherein said promoter is a promoter that directs expression in tapetum cells, anther epidermal cells or tapetum and anther epidermal cells.

88. The chimeric gene of claim 80, wherein said first promoter is PTA29, PTA13 or PTA26.

89. A plant cell comprising the chimeric gene of claim 80.

90. A plant or a seed of a plant comprising the chimeric gene of claim 80.

* * * * *

UNITED STATES PATENT AND TRADEMARK OFFICE
CERTIFICATE OF CORRECTION

PATENT NO. : 5,792,929
DATED : August 11, 1998
INVENTOR(S) : Mariani et al

It is certified that error appears in the above-identified patent and that said Letters Patent is hereby corrected as shown below:

Column 2, line 19, between "process" and "for" please delete "is".

Column 4, line 23, please replace "crops-pollination" by --cross-pollination--.

Column 9, line 38, please replace "embyo" with --embryo--.

Column 18, line 54, please replace "FH/fh" with --FH1/fh--.

Column 19, line 4, please replace "fertility restorer" with --fertility-restorer--.

Column 19, line 19, before "xC" please insert --RH2;SH1/*sh*-- in *superscript* instead of subscript.

In the Claims:

Claim 1, line 9, replace "fertility restorer" with --fertility-restorer--.

Claim 43, line 45, replace "a first foreign DNA" with --the first foreign DNA--.

Signed and Sealed this

Twenty-ninth Day of May, 2001

Attest:

NICHOLAS P. GODICI

Attesting Officer        Acting Director of the United States Patent and Trademark Office